United States Patent
Zhou et al.

(10) Patent No.: US 11,098,104 B2
(45) Date of Patent: Aug. 24, 2021

(54) PEGYLATED ENDOSTATIN ANALOGUE AND APPLICATION THEREOF

(71) Applicant: BEIJING PROTGEN LTD., Beijing (CN)

(72) Inventors: Daifu Zhou, Beijing (CN); Wenchao Wang, Beijing (CN); Hui Li, Beijing (CN); Guodong Chang, Beijing (CN)

(73) Assignee: BEIJING PROTGEN LTD., Beijing (CN)

( * ) Notice: Subject to any disclaimer, the term of this patent is extended or adjusted under 35 U.S.C. 154(b) by 3 days.

(21) Appl. No.: 16/349,191

(22) PCT Filed: Nov. 10, 2017

(86) PCT No.: PCT/CN2017/110532
§ 371 (c)(1),
(2) Date: May 24, 2019

(87) PCT Pub. No.: WO2018/086603
PCT Pub. Date: May 17, 2018

(65) Prior Publication Data
US 2020/0270333 A1    Aug. 27, 2020

(30) Foreign Application Priority Data
Nov. 10, 2016   (CN) .......................... 201610997233.2

(51) Int. Cl.
| | | |
|---|---|---|
| *A61K 47/00* | (2006.01) | |
| *C07K 14/78* | (2006.01) | |
| *A61K 47/58* | (2017.01) | |
| *A61K 38/00* | (2006.01) | |

(52) U.S. Cl.
CPC .............. *C07K 14/78* (2013.01); *A61K 47/58* (2017.08); *A61K 38/00* (2013.01)

(58) Field of Classification Search
CPC ........ C07K 14/78; C07K 14/47; A61K 47/58; A61K 38/00; A61K 47/00; A61K 38/17; A61K 47/60; A61P 35/00; A61P 43/00
See application file for complete search history.

(56) References Cited

U.S. PATENT DOCUMENTS

2010/0285103 A1*  11/2010  Luo .................... A61K 38/363
                                                    424/450

FOREIGN PATENT DOCUMENTS

CN          101596320 A      12/2009

OTHER PUBLICATIONS

Medical news (Year: 2020).*
Sridhar et al. Targeting angiogenesis: a review of angiogenesis inhibitors in the treatment of lung cancer. 2003. Lung Cancer (2003) 42, S81-S91.(Year: 2003).*
Walia et al. Endostatin's Emerging Roles in Angiogenesis, Lymphangiogenesis, Disease, and Clinical Applications. 2015. Biochim Biophys Acta. Dec. 2015; 1850(12): 2422-2438 (Year: 2015).*
Poluzz et al. Endostatin and endorepellin: a common route of action for similar angiostatic cancer avengers. 2016. Adv Drug Deliv Rev. Feb. 1, 2016; 97: 156-173. (Year: 2016).*
Medical news. 2020 (Year: 2020).*
Merck Manual consumer version—Cancer treatment. 2018 (Year: 2018).*
Merck Manual consumer version—Cancer therapy. 2018 (Year: 2018).*
NCI—Cancer (Year: 2020).*
NCI-2—Cancer (Year: 2020).*
Payne et al. Product development issues for PEGylated proteins. 2011. Pharmaceutical Development and Technology, 2011; 16(5): 423-440 (Year: 2011).*
Nie et al. Preparation and Stability of N-Terminal Mono-PEGylated Recombinant Human Endostatin. 2006.Bioconjugate Chem. 2006, 17, 995-999 (Year: 2006).*

* cited by examiner

*Primary Examiner* — James H Alstrum-Acevedo
*Assistant Examiner* — Mercy H Sabila
(74) *Attorney, Agent, or Firm* — Klarquist Sparkman, LLP

(57) ABSTRACT

The present invention provides a polyethylene glycol-modified endostatin analogue and an application thereof. The endostatin analogue is coupled to polyethylene glycol at lysine away from a nucleolin binding domain, or is coupled to polyethylene glycol at lysine away from a nucleolin binding domain and amidogen at the N end.

19 Claims, 9 Drawing Sheets

Specification includes a Sequence Listing.

Naturally occurring human endostatin (SEQ ID NO. 1)

```
         10         20         30         40         50         60
MHSHRDFQPV LHLVALNSPL SGGMRGIRGA DFQCFQQARA VGLAGTFRAF LSSRLQDLYS
         70         80         90        100        110        120
IVRRADRAAV PIVNLKDELL FPSWEALFSG SEGPLX1PGAR IFSFNGX2DVL THPTWPQX3SV
        130        140        150        160        170        180
WHGSDPNGRR LTESYCETWR TEAPSATGQA YSLLGGRLLG QSAASCHHAY IVLCIENSFM
```

TASX4

Endostatin K1 analogue (SEQ ID NO. 2)

```
         10         20         30         40         50         60
MHSHRDFQPV LHLVALNSPL SGGMRGIRGA DFQCFQQARA VGLAGTFRAF LSSRLQDLYS
         70         80         90        100        110        120
IVRRADRAAV PIVNLKDELL FPSWEALFSG SEGPLKPGAR IFSFDGKDVL RHPTWPQKSV
        130        140        150        160        170        180
WHGSDPNGRR LTESYCETWR TEAPSATGQA SSLLGGRLLG QSAASCHHAY IVLCIENSFM
```

TASK

Endostatin K2 analogue (SEQ ID NO. 3)

```
         10         20         30         40         50         60
MHSHRDFQPV LHLVALNSPL SGGMRGIRGA DFQCFQQARA VGLAGTFRAF LSSRLQDLYS
         70         80         90        100        110        120
IVRRADRAAV PIVNLX1DELL FPSWEALFSG SEGPLKPGAR IFSFNGX2DVL THPTWPQX3SV
        130        140        150        160        170        180
WHGSDPNGRR LTESYCETWR TEAPSATGQA YSLLGGRLLG QSAASCHHAY IVLCIENSFM
```

TASX4

FIG. 8A

Endostatin K3 analogue (SEQ ID NO. 4)

```
         10         20         30         40         50         60
MHSHRDFQPV LHLVALNSPL SGGMRGIRGA DFQCFQQARA VGLAGTFRAF LSSRLQDLYS
         70         80         90        100        110        120
IVRRADRAAV PIVNLX1DELL FPSWEALFSG SEGPLX2PGAR IFSFNGKDVL THPTWPQX3SV
        130        140        150        160        170        180
WHGSDPNGRR LTESYCETWR TEAPSATGQA YSLLGGRLLG QSAASCHHAY IVLCIENSFM

TASX4
```

Endostatin K4 analogue (SEQ ID NO. 5)

```
         10         20         30         40         50         60
MHSHRDFQPV LHLVALNSPL SGGMRGIRGA DFQCFQQARA VGLAGTFRAF LSSRLQDLYS
         70         80         90        100        110        120
IVRRADRAAV PIVNLX1DELL FPSWEALFSG SEGPLX2PGAR IFSFNGX3DVL THPTWPQKSV
        130        140        150        160        170        180
WHGSDPNGRR LTESYCETWR TEAPSATGQA YSLLGGRLLG QSAASCHHAY IVLCIENSFM

TASX4
```

Endostatin ESC analogue (SEQ ID NO. 6)

```
         10         20         30         40         50         60
MHSHRDFQPV LHLVALNSPL SGGMRGIRGA DFQCFQQARA VGLAGTFRAF LSSRLQDLYS
         70         80         90        100        110        120
IVRRADR

Endostatin NK1 analogue (SEQ ID NO. 7)

```
         10         20         30         40         50         60
MGGSHHHHHH SHRDFQPVLH LVALNSPLSG GMRGIRGADF QCFQQARAVG LAGTFRAFLS
         70         80         90        100        110        120
SRLQDLYSIV RRADRAAVPI VNLKDELLFP SWEALFSGSE GPLX1PGARIF SFNGX2DVLTH
        130        140        150        160        170        180
PTWPQX3SVWH GSDPNGRRLT ESYCETWRTE APSATGQAYS LLGGRLLGQS AASCHHAYIV
        190
LCIENSFMTA SX4
```

Endostatin NK2 analogue (SEQ ID NO. 8)

```
         10         20         30         40         50         60
MGGSHHHHHH SHRDFQPVLH LVALNSPLSG GMRGIRGADF QCFQQARAVG LAGTFRAFLS
         70         80         90        100        110        120
SRLQDLYSIV RRADRAAVPI VNLX1DELLFP SWEALFSGSE GPLKPGARIF SFNGX2DVLTH
        130        140        150        160        170        180
PTWPQX3SVWH GSDPNGRRLT ESYCETWRTE APSATGQAYS LLGGRLLGQS AASCHHAYIV
        190
LCIENSFMTA SX4
```

Endostatin NK3 analogue (SEQ ID NO. 9)

```
         10         20         30         40         50         60
MGGSHHHHHH SHRDFQPVLH LVALNSPLSG GMRGIRGADF QCFQQARAVG LAGTFRAFLS
         70         80         90        100        110        120
SRLQDLYSIV RRADRAAVPI VNLX1DELLFP SWEALFSGSE GPL X2PGARIF SFNGKDVLTH
        130        140        150        160        170        180
PTWPQX3SVWH GSDPNGRRLT ESYCETWRTE APSATGQAYS LLGGRLLGQS AASCHHAYIV
        190
LCIENSFMTA SX4
```

FIG. 8C

Endostatin NK4 analogue (SEQ ID NO. 10)

```
          10         20         30         40         50         60
MGGSHHHHHH SHRDFQPVLH LVALNSPLSG GMRGIRGADF QCFQQARAVG LAGTFRAFLS
          70         80         90        100        110        120
SRLQDLYSIV RRADRAAVPI VNLX₁DELLFP SWEALFSGSE GPLX₂PGARIF SFNGX₃DVLTH
         130        140        150        160        170        180
PTWPQKSVWH GSDPNGRRLT ESYCETWRTE APSATGQAYS LLGGRLLGQS AASCHHAYIV
         190
LCIENSFMTA SX₄
```

Endostatin NESC analogue (SEQ ID NO. 11)

```
          10         20         30         40         50         60
MGGSHHHHHH SHRDFQPVLH LVALNSPLSG GMRGIRGADF QCFQQARAVG LAGTFRAFLS
          70         80         90        100        110        120
SRLQDLYSIV RRADRAAVPI VNLKDELLFP SWEALFSGSE GPLKPGARIF SFDGKDVLRH
         130        140        150        160        170        180
PTWPQKSVWH GSDPNGRRLT ESYCETWRTE APSATGQASS LLGGRLLGQS AASCHHAYIV
         190
LCIENSFMTA SKC
```

Endostatin ESK analogue (SEQ ID NO. 12)

```
          10         20         30         40         50         60
MHSHRDFQPV LHLVALNSPL SGGMRGIRGA DFQCFQQARA VGLAGTFRAF LSSRLQDLYS
          70         80         90        100        110        120
IVRRADRAAV PIVNLX₁DELL FPSWEALFSG SEGPLX₂PGAR IFSFNGX₃DVL THPTWPQX₄SV
         130        140        150        160        170        180
WHGSDPKGRR LTESYCETWR TEAPSATGQA YSLLGGRLLG QSAASCHHAY IVLCIENSFM

TASX₅
```

FIG. 8D

Endostatin NESK analogue (SEQ ID NO. 13)

```
         10         20         30         40         50         60
MGGSHHHHHH SHRDFQPVLH LVALNSPLSG GMRGIRGADF QCFQQARAVG LAGTFRAFLS
         70         80         90        100        110        120
SRLQDLYSIV RRADRAAVPI VNLX₁DELLFP SWEALFSGSE GPLX₂PGARIF SFNGX₃DVLTH
        130        140        150        160        170        180
PTWPQX₄SVWH GSDPKGRRLT ESYCETWRTE APSATGQAYS LLGGRLLGQS AASCHHAYIV
        190
LCIENSFMTA SX₅
```

FIG. 8E

PEGYLATED ENDOSTATIN ANALOGUE AND APPLICATION THEREOF

CROSS REFERENCE TO RELATED APPLICATIONS

This is the U.S. National Stage of International Application No. PCT/CN2017/110532, filed Nov. 10, 2017, which was published in Chinese, which in turn claims the benefit of Chinese Patent Application No. 201610997233.2, filed on Nov. 10, 2016.

FIELD OF THE INVENTION

The present invention relates to new recombinant protein drugs. In particular, the present invention relates to pegylated endostatin analogues and applications thereof.

BACKGROUND OF THE INVENTION

Neoangiogenesis refers to the generation of new capillaries on the original blood vessels. Tumor growth and migration depend on the generation of new blood vessels, and by using microvascular endothelial cells in tumor as target for cancer treatment, it provides a therapeutic means for the treatment of tumor (Folkman J N Engl J Med 1971; 285: 1182-1186).

Endostatin is an enzymatically digested product with a molecular weight of 20 kDa, derived from the C-terminus of type XVIII collagen. In 1997, Professor Judah Folkman et al. from Harvard University found this protein in the medium of hemangioendothelioma cells, which had the activity of inhibiting proliferation, migration and in vivo angiogenesis of vascular endothelial cells. It was found by further experimentations that recombinant endostatin could inhibit the growth and migration of various tumors in mice, even cure tumors completely, and did not produce drug resistance. The mechanism concerning how it works is that it inhibits the generation of new blood vessels surrounding tumor tissues by inhibiting the growth of vascular endothelial cells, which makes the tumor tissues unable to get a large amount of nutrients and oxygen as required for growth, finally resulting in growth stopping or necrosis (Folkman J et al. Cell 1997; 88:277-285; Folkman J. et al. Nature 1997; 390: 404-407). In 2010, Professor Luo Yongzhang et al. from Tsinghua University found that endostatin could also significantly inhibit tumor-related lymphangiogenesis (Yongzhang Luo. et al., *Journal of Pathology* 2010; 222: 249-260; Yongzhang Luo. *Front. Med.* 2011, 5: 336-340). Recombinant human endostatin prepared by genetic engineering can be used as a drug for tumor treatment, and its clinical experiments show that it can effectively inhibit tumor growth. In China, clinical trials with non-small cell lung cancer as the main indication have shown its prominent therapeutic effect on tumor.

For many years, tumor treatment mainly depends on small-molecule compound therapy (chemotherapy) and radiotherapy. Although both methods are very effective, there are also some toxic side effects. In contrast, protein drugs have less toxic side effects and do not produce drug resistance, however, the employment of gastrointestinal administration would result in a severe first pass effect. In order to achieve the highest activity in vivo, to improve bioavailability, and to reduce drug degradation in vivo, protein drugs are usually administered by means of intravenous or subcutaneous injection. For proteins with a small molecular weight, their half-life is generally short after intravenous administration. One of the important reasons is that small-molecule proteins can be quickly eliminated by means of renal filtration. Proteins, with a hydraulic radius in blood greater than that of albumin or with a molecular weight greater than 66,000 Daltons (66 kDa), generally can be stably retained in the circulatory system, while small-molecule protein drugs are rapidly eliminated by glomerular filtration. Therefore, in order to maintain an effective treatment concentration in blood, patients need to receive injections or intravenous drips frequently. Although this treatment means can achieve the therapeutic purpose, it brings serious inconvenience and pain to patients, also seriously affects patient's compliance with drug treatment, and also increases the cost of medication. Moreover, the long-term frequent use of some drugs may also have some side effects, such as an immune response.

Endostatin as a protein drug also has the disadvantages of short half-life and high clearance in vivo. At present, the main clinical means of medication is frequent administration (in general, daily administration) to maintain an effective blood concentration, and long-term medication is required, which generates large mental and economic burdens on patients. An object of the present invention is to improve the in vivo metabolic characteristics of the protein, so that it has higher stability and longer half-life in vivo, even higher therapeutic effects, thereby achieving the purposes of reducing the frequency of administration, reducing the cost of medication, and reducing economic burden on patients.

Modification of proteins with high molecular-weight polymers is a common method of changing and controlling the kinetic properties of drugs such as half-life, immunological characteristics and toxicological properties. Among them, polyethylene glycol (PEG) is the most widely used amphiphilic high molecular-weight polymer. PEG has the characteristics of good solubility, good biocompatibility, non-toxicity and no immunogenicity, and is a polymer that can be used in drug preparation as approved by drug administration institutions in many countries and regions, including FDA in USA and SFDA in China Coupling proteins with hydrophilic polymers such as PEG can reduce proteolysis, enhance protein stability, and reduce non-specific adsorption and antigenicity; when the hydraulic radius of the coupled product reaches the lower limit of glomerular filtration, the efficiency of renal clearance can be reduced greatly; this is an effective method for prolonging the half-life of protein drugs in vivo (Gianfranco Pasut et al. Advanced Drug Delivery Reviews 60 (2008) 69-78; F. M. Veronese et al. Milestones in Drug Therapy 2009, 11-31). With the development of PEG modification technology, a variety of groups on protein molecules can be modified by PEG to meet different demands. For example, proteins or polypeptides can be modified randomly by modifiers of monomethoxy polyethylene glycol succinimidyl active esters (such as mPEG-SC, mPEG-SCM, mPEG-SPA, and mPEG-NHS) at N-terminal α-amino group or at lysine side-chain ε-amino group, so as to achieve the modification of proteins at multiple sites. Monomethoxy polyethylene glycol aldehyde (mPEG-Aldehyde) can specifically react with the N-terminal α-amino group of a protein or a polypeptide under weak acidic conditions to form an unstable Schiff base that is further reduced by sodium cyanoborohydride to produce a stable secondary amine, thereby achieving site-directed modification at N-terminus. The free cysteines of proteins or polypeptides are selectively modified by modifiers of monomethoxy polyethylene glycol maleimides (such as mPEG-MAL and mPEG2-MAL). Up to now, PEG modification technology has been successfully applied to a variety of proteins. The marketed PEG-modified protein drugs, which have been approved by FDA, include PEG-adenosine deiminase (1990), PEG-asparaginase (1994), PEG-α2b interferon (2001), PEG-granulocyte colony-stimulating factor (2002), PEG-α2a interferon (2002), PEG-α2a interferon-ribavirin mixed preparation (2004), PEG-erythropoietin (2007), PEG-TNFα antibody (2008), PEG-α2b interferon-ribavirin mixed preparation (2008), PEG-urate oxidase (2010). Representative PEG-modified protein drugs undergoing clinical research include PEG-arginine deiminase (Polaris Group, Phase III), PEG-growth hormone (Changchun Gensci Pharmaceutical Co., Ltd., Phase III), PEG-β1a interferon (Biogen Idec, Phase III), etc.

In addition to PEG that can be used to modify proteins to prolong the half-life of drugs, other polymer modifiers can also be used, for example, dextran, polysucrose, starch, polyalanine, copolymer of oxalic acid and malonic acid, carboxymethyl cellulose, polyvinylpyrrolidone, poly(2-alkoxy-1,3-propanediol), copolymer of ethylene and maleic hydrazide, polysialic acid, cyclodextrin, etc.

SUMMARY OF THE INVENTION

The inventors discovered that protein activity can be significantly enhanced by coupling PEG to endostatin at lysine distant from nucleolin binding domain, therefore, the present invention provides a PEG-modified endostatin analogue that is coupled to PEG at lysine distant from nucleolin binding domain, thereby enhancing its bioactivity of inhibiting tumor cell migration. The PEG-modified endostatin analogue according to the present invention has higher stability and longer half-life in vivo than unmodified endostatin, and has a significantly enhanced activity of inhibiting neoangiogenesis.

In a first aspect, the present invention provides an endostatin analogue-PEG coupled complex, wherein the endostatin analogue has a lysine residue at a position corresponding to position 96 of the amino acid sequence SEQ ID NO. 1 of naturally occurring endostatin, and no lysine residue at any other position; and the endostatin analogue is coupled to PEG only at the lysine residue.

In a second aspect, the present invention provides an endostatin analogue-PEG coupled complex, wherein the endostatin analogue has a lysine residue at a position corresponding to position 96 of the amino acid sequence SEQ ID NO. 1 of naturally occurring endostatin, and no lysine residue at any other position; and the endostatin analogue is coupled to PEG at N-terminus and the lysine residue.

In preferred embodiments, in the complex according to the first aspect and the second aspect, the endostatin analogue is formed by mutation of lysine residues at positions 76, 107, 118 and 184 of the amino acid sequence SEQ ID NO. 1 of naturally occurring endostatin. In a particular embodiment, the sequence of the endostatin analogue is set forth in SEQ ID NO. 3.

In a third aspect, the present invention provides an endostatin analogue-PEG coupled complex, wherein the endostatin analogue has a lysine residue at a position corresponding to position 96 of the amino acid sequence SEQ ID NO. 1 of naturally occurring endostatin, and no lysine residue at any other position; and the endostatin analogue has an amino acid sequence inserted at its N-terminus; and the endostatin analogue is coupled to PEG only at the lysine residue.

In a fourth aspect, the present invention provides an endostatin analogue-PEG coupled complex, wherein the endostatin analogue has a lysine residue at a position corresponding to position 96 of the amino acid sequence SEQ ID NO. 1 of naturally occurring endostatin, and no lysine residue at any other position; and the endostatin analogue has an amino acid sequence inserted at its N-terminus; and the endostatin analogue is coupled to PEG at N-terminus and the lysine residue.

In preferred embodiments, in the complex according to the third aspect and the fourth aspect, the endostatin analogue is formed by mutation of the lysine residues at positions 76, 107, 118 and 184 of the amino acid sequence SEQ ID NO. 1 of naturally occurring endostatin, and insertion of an amino acid sequence at its N-terminus. In more preferred embodiments, the inserted amino acid sequence is GGSHHHHH (SEQ ID NO. 14) inserted between methionine M and histidine H at the N-terminus. In more preferred embodiments, the sequence of the endostatin analogue is set forth in SEQ ID NO. 8.

In preferred embodiments, in the endostatin analogue of the coupled complex according to the present invention, the lysine residues at positions 76, 107, 118 and 184 of the amino acid sequence SEQ ID NO. 1 of naturally occurring endostatin are mutated to X1, X3, X4 and X5, respectively, wherein X1, X3, X4 or X5 is independently any naturally occurring amino acid other than lysine. X1, X3, X4 or X5 is independently a water-soluble amino acid preferably, is further preferably any one of charged amino acids: arginine, histidine, glutamic acid and aspartic acid, is further preferably any one of positively charged amino acids: arginine and histidine, and is most preferably arginine.

In preferred embodiments, in the complex according to the present invention, the amino acid sequence inserted at the N-terminus of endostatin analogue is MGGSHHHHH (SEQ ID NO. 15).

In preferred embodiments, in the complex according to the present invention, endostatin analogue is coupled to PEG via covalent bond.

In preferred embodiments, the PEG has an average molecular weight between 5,000 and 40,000 Daltons.

In more preferred embodiments, the PEG has an average molecular weight between 20,000 and 40,000 Daltons.

In preferred embodiments, the PEG is monomethoxy polyethylene glycol, monoglucose polyethylene glycol or monogalactose polyethylene glycol.

In preferred embodiments, the PEG is linear or branched.

In preferred embodiments, the PEG is monomethoxy polyethylene glycol.

In some embodiments, PEG is coupled to endostatin analogue at an amino group.

In some embodiments, PEG is coupled to endostatin analogue at lysine side-chain ε-amino group.

In some embodiments, PEG is coupled to endostatin analogue at N-terminal α-amino group and ε-amino group of lysine residue.

In more preferred embodiments, the coupling reaction between PEG and the amino group of endostatin analogue is carried out by using monomethoxy polyethylene glycol propionaldehyde (mPEG-ALD), monomethoxy polyethylene glycol butyraldehyde (mPEG-ButyrALD), monomethoxy polyethylene glycol succinimidyl carbonate (mPEG-SC), monomethoxy polyethylene glycol succinimidyl acetate (mPEG-SCM), monomethoxy polyethylene glycol succinimidyl propionate (mPEG-SPA), monomethoxy polyethene glycol succinimidyl butyrate (mPEG-SBA), monomethoxy polyethylene glycol succinimidyl α-methyl-butyrate (mPEG-SMA), monomethoxy polyethylene glycol N-hydroxylsuccinimide (mPEG-NHS).

The present invention further provides a pharmaceutical composition, comprising the endostatin analogue-PEG coupled complex according to the present invention and a pharmaceutically acceptable carrier.

The present invention further provides a method for treating a disease caused by neoangiogenesis or neolymphangiogenesis, comprising administering to a patent the endostatin analogue-PEG coupled complex or the pharmaceutical composition according to the present invention.

The present invention further provides use of the endostatin analogue-PEG coupled complex or the pharmaceutical composition according to the present invention for treatment of a disease caused by neoangiogenesis or neolymphangiogenesis.

In preferred embodiments, the disease caused by neoangiogenesis or neolymphangiogenesis is tumor.

The present invention further provides use of the coupled complex according to the present invention for preparation of a medicament for inhibiting neoangiogenesis or neolymphangiogenesis in vivo or in vitro.

When the complex according to the present invention is used for inhibiting neoangiogenesis or neolymphangiogenesis in vivo, its half-life is significantly prolonged as compared with endostatin, and its inhibition rate is significantly enhanced as compared with endostatin under the same administration conditions.

BRIEF DESCRIPTION OF THE DRAWINGS

FIGS. 8A-8E: sequences of the endostatin analogues as involved in the present invention.

SEQUENCE LISTING

Figure 1:
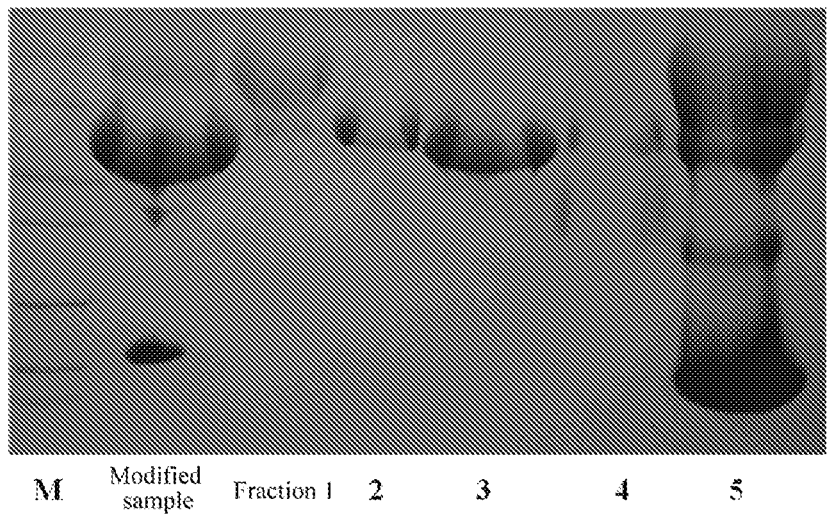
FIG. 1: the result of SDS-PAGE electrophoresis analysis of the modified sample in which endostatin is single-modified with 20 kDa mPEG-ALD at N-terminus, and of the subsequent samples after chromatographic purification. Lane 1 represents low molecular weight standards of 116, 66, 45, 30, 25, 18.4, 14.4 kDa from top to bottom; Lane 2 represents the sample in which endostatin is modified with 20 kDa mPEG-ALD; Lanes 3~7 represent Fractions 1, 2, 3, 4 and 5 obtained by elution with 100, 150, 200, 350 and 500 mM NaCl in chromatographic purification, respectively, wherein the 200 mM NaCl eluted fraction (Fraction 3) of Lane 5 is the fraction of the N-terminal single-modification product.

The Sequence Listing is submitted as an ASCII text file in the form of the file named "Sequence.txt" (~28 Kb), which was created on Jan. 29, 2020, which is incorporated by reference herein.

DETAILED DESCRIPTION OF THE INVENTION

The term "endostatin (ES)" as used herein may refer to naturally occurring endostatin, preferably human endostatin, which, for example, has but is not limited to a sequence of SEQ ID NO. 1; for example, may also be naturally occurring endostatin from other mammals such as mouse, rat, pig, dog, rabbit, sheep, goat, cat, etc. "Endostatin" may also refer to functional variants of endostatin, for example, engineered functional variants, which differ from naturally occurring endostatin by substitution, deletion or addition of one or more amino acids, and have substantively the same biological function, such as activity of inhibiting proliferation, migration and angiogenesis in vivo of vascular endothelial cells. "Endostatin" may also refer to derivatives or modified products of naturally occurring endostatin or functional variants thereof, for example, PEG-modified products.

The term "functional variant" as used herein include mutants of endostatin which comprise substitution, deletion or addition of one or more (e.g. 1-5, 1-10 or 1-15, particularly, such as 1, 2, 3, 4, 5, 6, 7, 8, 9, 10, 11, 12 or even more) amino acids in the amino acid sequence, and the mutants have similar biological activity of inhibiting proliferation, migration and angiogenesis in vivo of vascular endothelial cells as endostatin. The biological activity of "functional variant" of endostatin may be, for example 30% or higher, 50% or higher, 60% or higher, 70% or higher, 80% or higher, or 90% or higher of that of naturally occurring endostatin, such as naturally occurring human endostatin. The "functional variant" may be naturally occurring mutants, or may also be artificial mutants, for example, mutants obtained by site-directed mutagenesis, or mutants produced by genetic recombination method.

The biological activity of the "functional variant" may be determined by a method for detecting endostatin activity as well known in the art. For example, HMEC (human mammary epithelial cells) may be selected, Migration (Tranwell Assay) assay is used to analyze the inhibition rate of functional variants for HMEC migration, and the number of cells is counted to reflect protein activity (see Luo yongzhang et al., Endostatin inhibits tumourlymphangiogenesis and lymphatic metastasis via cell surface nucleolin on lymphangiogenic endothelial cells (J Pathol 2010; 222: 249-260).

In the present invention, "endostatin analogue" and "endostatin functional variant" can be used interchangeably. In some embodiments, "endostatin analogue" according to the present invention has a lysine residue at a position corresponding to position 96 of naturally occurring human endostatin (e.g. SEQ ID NO. 1), and no lysine residue at any other position, so that PEG can only be coupled to the endostatin analogue at the lysine residue or be coupled simultaneously at N-terminus and the lysine residue, without being coupled at any other amino acid residue. The coupled complex thus obtained has higher stability and longer half-live in vivo, and has its activity of inhibiting neoangiogenesis significantly enhanced, as compared with naturally occurring human endostatin or a complex in which naturally occurring human endostatin is coupled to single PEG at N-terminus.

Endostatin analogues according to the present invention can be obtained by engineering naturally occurring endostatin (e.g. naturally occurring human endostatin or naturally occurring mammalian endostatin), in particular, are endostatin analogues obtained by mutating the lysine residues at positions 76, 107, 118 and 184, and only reserving the lysine residue at position 96, in naturally occurring human endostatin (e.g. SEQ ID NO. 1), or endostatin analogues obtained by mutating the lysine residues at positions corresponding to positions 76, 107, 118, 184 of naturally occurring human endostatin (e.g. SEQ ID NO. 1), and only reserving the lysine residue at a position corresponding to position 96 of naturally occurring human endostatin (e.g. SEQ ID NO. 1), in naturally occurring other mammalian endostatin. Endostatin analogues according to the present invention may also be obtained by engineering naturally occurring or artificially synthesized functional variants of endostatin as known, in particular, if a functional variant of endostatin has a lysine residue at a position corresponding to position 96 of naturally occurring endostatin, the lysine residue is kept unchanged, and all the other lysine residues of the functional variant of endostatin are mutated; if a functional variant of endostatin does not have a lysine residue at a position corresponding to position 96 of naturally occurring endostatin, the amino acid at the position is mutated to a lysine residue, and all the other lysine residues of the functional variant of endostatin are mutated.

Functional variants of endostatin, which can be engineered so as to obtain the endostatin analogues according to the present invention, include ES variants produced by random deletion of the first amino acid M when human ES is recombinantly expressed in E. coli. Functional variants of endostatin, which can be engineered so as to obtain the endostatin analogues according to the present invention, also include ES variants having 4 amino acids deleted at N-terminus, produced by random cleavage at N-terminus when ES is recombinantly expressed in yeast. Functional variants of endostatin, which can be engineered so as to obtain the endostatin analogues according to the present invention, include YH-16, which is a ES variant obtained by addition of 9 additional amino acids (MGGSHHHHH, SEQ ID NO. 15) at N-terminus of ES, for the convenience of enhancing soluble expression and facilitating purification (Fu Y et al. IUBMB Life 2009; 61: 613-626; Wang Jet al. Zhongguo fei ai za zhi 2005; 8: 283-290; Han B et al. J Thorac Oncol 2011; 6(6): 1104-1109, which is incorporated herein by reference in its entirety). Functional variants of endostatin, which can be engineered so as to obtain the endostatin analogues according to the present invention, also include the endostatin mutants as disclosed in PCT international application PCT/CN2012/081210, such as ES006, ES008, ES011, S02, S09, Z006, Z008, ZN1, etc. (which is incorporated herein by reference in its entirety). Functional variants of endostatin, which can be engineered so as to obtain the endostatin analogues according to the present invention, further include the endostatin mutants as disclosed in PCT international publication No. WO2016/070798, such as 003, 007, Z101, 009, S03, 36, 249, 381, 57, 114, 124, 125, 160, 163, 119 (which is incorporated herein by reference in its entirety).

The expression "position corresponding to amino acid sequence SEQ ID NO. 1 of naturally occurring endostatin" as described in the present invention refers to the position in a functional variant of endostatin that corresponds to the corresponding amino acid residue in SEQ ID NO. 1, after alignment of the functional variant of endostatin with the amino acid sequence SEQ ID NO. 1 of naturally occurring endostatin by using software or algorithm as well known in the art. The software or algorithm includes, but is not limited to BLAST, FASTA.

The term "polyethylene glycol (PEG)" as used in the present invention may be monomethoxy polyethylene glycol, monoglucose polyethylene glycol or monogalactose polyethylene glycol. The PEG used may be linear or branched, and may have a molecular weight of, for example, about 5 kD to about 50 kD, about 20 kD to about 40 kD or such as about 20 kD.

The term "PEG modification" or "PEG coupling" as used herein may refer to chemically coupling PEG modifier molecule(s) to a protein molecule, the group of the PEG modifier involved in the coupling reaction is an active group introduced during its activation, and the group of the protein is mainly a free amino group, a thiol group or the like therein, preferably an amino group. Coupling with polyethylene glycol (PEG) can prolong the half-life of the coupled complex in vivo, avoid degradation by protease or enhance solubility. Methods for modifying proteins with PEG are well known to those skilled in the art.

The term "PEG modifier" includes, but is not limited to monomethoxy PEG modifier, which is an activated PEG obtained by blocking the hydroxyl group of a PEG molecule at one end with a methoxy group and activating the hydroxyl group at the other end by a suitable activation method. Since the reactivity of a hydroxyl group itself is very low, the reactivity of the activated PEG molecule is greatly improved, called "PEG modifier". With respect to the selection of activating groups, the mechanism concerning activation, and the mechanism concerning the modification reaction of PEG modifiers obtained by activation, they are well known in the art and have been reported in many documents. PEG modifiers are commercially available. Useful PEG modifiers include, but are not limited to monomethoxy polyethylene glycol propionaldehyde (mPEG-ALD), monomethoxy polyethylene glycol butyraldehyde (mPEG-ButyrALD), monomethoxy polyethylene glycol succinimidyl carbonate (mPEG-SC), monomethoxy polyethylene glycol succinimidyl acetate (mPEG-SCM), monomethoxy polyethylene glycol succinimidyl propionate (mPEG-SPA), monomethoxy polyethene glycol succinimidyl butyrate (mPEG-SBA), monomethoxy polyethylene glycol succinimidyl α-methylbutyrate (mPEG-SMA), monomethoxy polyethylene glycol N-hydroxylsuccinimide (mPEG-NHS).

In the present invention, PEG is coupled to an endostatin analogue at an amino group, for example, is coupled to an endostatin analogue at lysine side-chain ε-amino group, or is coupled to an endostatin analogue at N-terminal α-amino group and at the ε-amino group of lysine residue.

As described in the present invention (e.g. Examples), endostatin K1 analogue refers to an endostatin analogue with an amino acid sequence of SEQ ID NO. 2, obtained by mutation of the lysine residues at positions 96, 107, 118, and 184 starting from the N-terminus of the amino acid sequence SEQ ID NO. 1 of endostatin to X2, X3, X4 and X5, respectively, wherein X2, X3, X4 or X5 is any naturally occurring amino acid other than lysine, is preferably a water-soluble amino acid, is further preferably one of charged amino acids: arginine, histidine, glutamic acid and aspartic acid, is further preferably one of positively charged amino acids: arginine and histidine, and is most preferably arginine.

As described in the present invention (e.g. Examples), endostatin K2 analogue refers to an endostatin analogue with an amino acid sequence of SEQ ID NO. 3, obtained by mutation of the lysine residues at positions 76, 107, 118 and 184 starting from the N-terminus of the amino acid sequence SEQ ID NO. 1 of endostatin to X1, X3, X4 and X5, respectively, wherein X1, X3, X4, or X5 is any naturally occurring amino acid other than lysine, is preferably a water-soluble amino acid, is further preferably one of charged amino acids: arginine, histidine, glutamic acid and aspartic acid, is further preferably one of positively charged amino acids: arginine and histidine, and is most preferably arginine.

As described in the present invention (e.g. Examples), endostatin K3 analogue refers to an endostatin analogue with an amino acid sequence of SEQ ID NO. 4, obtained by mutation of the lysine residues at positions 76, 96, 118 and 184 starting from N-terminus of the amino acid sequence SEQ ID NO. 1 of endostatin to X1, X2, X4 and X5, respectively, wherein X1, X2, X4, or X5 is any naturally occurring amino acid other than lysine, is preferably a water-soluble amino acid, is further preferably one of charged amino acids: arginine, histidine, glutamic acid and aspartic acid, is further preferably one of positively charged amino acids: arginine and histidine, and is most preferably arginine.

As described in the present invention (e.g. Examples), endostatin K4 analogue refers to an endostatin analogue with an amino acid sequence of SEQ ID NO. 5, obtained by mutation of the lysine residues at positions 76, 96, 107 and 184 starting from N-terminus of the amino acid sequence SEQ ID NO. 1 of endostatin to X1, X2, X3 and X5, respectively, wherein X1, X2, X3, or X5 is any naturally occurring amino acid other than lysine, is preferably a water-soluble amino acid, is further preferably one of charged amino acids: arginine, histidine, glutamic acid and aspartic acid, is further preferably one of positively charged amino acids: arginine and histidine, and is most preferably arginine.

As described in the present invention (e.g. Examples), endostatin ESC analogue refers to an endostatin analogue with an amino acid sequence of SEQ ID NO. 6, obtained by linkage of a cysteine residue C to C-terminus of the amino acid sequence SEQ ID NO. 1 of endostatin.

As described in the present invention (e.g. Examples), endostatin NK1, NK2, NK3, NK4, NESC analogues refer to endostatin analogues with amino acid sequences of SEQ ID NO. 7, SEQ ID NO. 8, SEQ ID NO. 9, SEQ ID NO. 10 and SEQ ID NO. 11, respectively. Endostatin NK1, NK2, NK3, NK4, NESC analogues are obtained by insertion of the amino acid sequence GGSHHHHH between methionine M and histidine H at N-terminus of said endostatin K1, K2, K3, K4, ESC analogues, respectively.

As described in the present invention (e.g. Examples), endostatin ESK analogue refers to an endostatin analogue with an amino acid sequence of SEQ ID NO. 12, obtained by mutation of the lysine residues at positions 76, 96, 107, 118 and 184 starting from N-terminus of the amino acid sequence SEQ ID NO. 1 of endostatin to X1, X2, X3, X4 and X5, respectively, and mutation of the asparagine residue at position 127 starting from N-terminus of the amino acid sequence SEQ ID NO. 1 of endostatin to lysine, wherein X1, X2, X3, X4, or X5 is any naturally occurring amino acid other than lysine, is preferably a water-soluble amino acid, is further preferably one of charged amino acids: arginine, histidine, glutamic acid and aspartic acid, is further preferably one of positively charged amino acids: arginine and histidine, and is most preferably arginine.

As described in the present invention (e.g. Examples), endostatin NESK analogue refers to an endostatin analogue with an amino acid sequence of SEQ ID NO. 13, obtained by insertion of the amino acid sequence GGSHHHHH between methionine M and histidine H at N-terminus of said endostatin ESK analogue.

The term "single modification" as used herein refers to a product obtained by modification of an endostatin or an endostatin analogue with one PEG molecule.

The term "dual modification" as used herein refers to a product obtained by modification of an endostatin or an endostatin analogue with two PEG molecules.

The present invention further provides a pharmaceutical composition, comprising the endostatin analogue-PEG coupled complex according to the present invention, for treating a disease caused by neoangiogenesis or neolymphangiogenesis. In some embodiments, said disease caused by neoangiogenesis or neolymphangiogenesis is tumor, including, but not limited to lung cancer, breast cancer, etc.

Suitably, the pharmaceutical composition further comprises a pharmaceutically acceptable carrier.

The term "pharmaceutically acceptable carrier" as used herein refers to substances such as solid or liquid diluents, fillers, antioxidants, and stabilizers, which can be administered safely. Depending on the route of administration, various carriers as well known in the art can be administered, including, but not limited to saccharides, starches, celluloses and derivatives thereof, maltose, gelatin, talc, calcium sulfate, vegetable oils, synthetic oils, polyols, alginic acid, phosphate buffer, emulsifier, isotonic saline, and/or pyrogen-free water.

Said pharmaceutical composition may also be a sustained-release preparation in a form selected from a microcapsule, a hydrogel, a microsphere, a micro-osmotic pump or a liposome.

The present invention further provides a kit comprising the endostatin analogue-PEG coupled complex according to the present invention and instructions for use.

The present invention further provides a method for treating a disease caused by neoangiogenesis or neolymphangiogenesis, comprising administering to a subject a therapeutically effective amount of the endostatin analogue-PEG coupled complex according to the present invention. In some embodiments, said disease caused by neoangiogenesis or neolymphangiogenesis is tumor, including, but not limited to lung cancer, breast cancer, colon cancer, etc.

The term "therapeutically effective amount" as used herein refers to an amount of an active compound that is sufficient to cause a biological or medical response in a subject as desired by the clinician. The "therapeutically effective amount" of an endostatin analogue-PEG coupled complex can be determined by those skilled in the art depending on factors such as route of administration, body weight, age and condition of a subject, and the like. For example, a typical daily dose may range from 0.01 mg to 100 mg of an active ingredient per kg of body weight.

The medicament provided by the present invention can be prepared into a clinically acceptable dosage form such as a powder or an injection. The pharmaceutical composition according to the present invention can be administered to a subject by any suitable route, for example, by routes such as oral administration, intravenous infusion, intramuscular injection, subcutaneous injection, subperitoneal administration, rectal administration, sublingual administration, or inhalation, transdermal administration, and the like.

Unless otherwise specified, the scientific and technical terms used in this specification shall have the meanings commonly understood by those skilled in the art. In general, the nomenclature and techniques associated with cell and tissue culture, molecular biology, immunology, microbiology, genetics, and protein and nucleic acid chemistry as used in this specification are well known and commonly used in the art.

Unless otherwise specified, the methods and techniques used in the present specification are generally carried out according to the well-known and conventional methods in the art and the various means as described in this specification or in the reference documents cited therein.

In the following examples, products resulted from single modification of endostatin and endostatin K1, K2, K3, K4, ESC, NK1, NK2, NK3, NK4, NESC, ESK, NESK analogues with PEG at N-terminal amino group, products resulted from dual modification thereof with PEG at N-terminal amino group and lysine amino group, products resulted from single modification thereof with PEG at lysine amino group, and products resulted from single modification thereof with PEG at C-terminal thiol, were prepared and purified, respectively, and were determined for their inhibition rates for HMEC migration. In the endostatin K1, K2, K3, K4, NK1, NK2, NK3, NK4, ESK, NESK analogues as used in the following examples, mutation of lysine refers to mutation of lysine to arginine.

EXAMPLES

Example 1: Coupling of 20 kDa PEG to Naturally Occurring Human Endostatin at N-Terminal Amino Group Naturally occurring human endostatin was dialyzed into a 30 mM sodium acetate solution (pH 5.0±1.0), the protein concentration was determined, and the protein concentration was adjusted to between 5 and 15 mg/ml. The amount of 20 kDa monomethoxy polyethylene glycol propionaldehyde (mPEG-ALD) to be added was calculated according to a molar ratio of the protein of interest to PEG of 1:3, and the amount of the reducing agent sodium cyanoborohydride was calculated according to the volume of the final solution, at a concentration of 20 mM. The desired monomethoxy polyethylene glycol propionaldehyde (mPEG-ALD) and sodium cyanoborohydride were weighed, added to the protein of interest, stirred homogeneously and then allowed to stand at room temperature for 6-8 hours. The electrophoresis graph of the modification result was shown in FIG. 1. Each band in the electrophoresis gel was subjected to content analysis by 1D gel quantification software Quantity One of Bio-Rad and was compared with molecular weight standards. The result showed that the percentage of single-modified endostatin (a product with a molecular weight of 40 kDa) was above 60%, i.e., an endostatin molecule was modified with a monomethoxy PEG molecule having a molecular weight of 20 kDa.

Example 2: Purification of the Product of Coupling 20 kDa PEG to Naturally Occurring Human Endostatin at N-Terminal Amino Group The solution of product of the coupling reaction between monomethoxy polyethylene glycol propionaldehyde (mPEG-ALD) and naturally occurring human endostatin in Example 1 was purified by a cation chromatographic column. SPFF medium (GE Healthcare) was particularly selected, the pH of the reaction solution was adjusted to 5.0~7.0, the cation column was equilibrated with 20 mM $NaH_2PO_4$ (pH adjusted to 5.0~7.0) and the sample was loaded. Gradient elution was carried out using 20 mM $NaH_2PO_4$, 500 mM NaCl (pH 5.0~7.0), and different fractions were collected according to ultraviolet absorptions at 280 nm. The SDS-PAGE analysis was carried out, and the analysis result was shown in FIG. 1. As seen from FIG. 1, Fraction 3 was the product (with a molecular weight of 40 kDa) resulted from single-modification of endostatin with 20 kDa PEG. Since the pKa values of N-terminal amino group and lysine side-chain amino group were 8.0 and 10.5, respectively, the reactivity of N-terminal amino group at pH 5.0±1.0 was $10^{(10.5-8.0)}=316$ times as much as the activity of lysine side-chain amino group. Therefore, the single-modification product could be considered as an N-terminal single-modification product.

Figure 2:
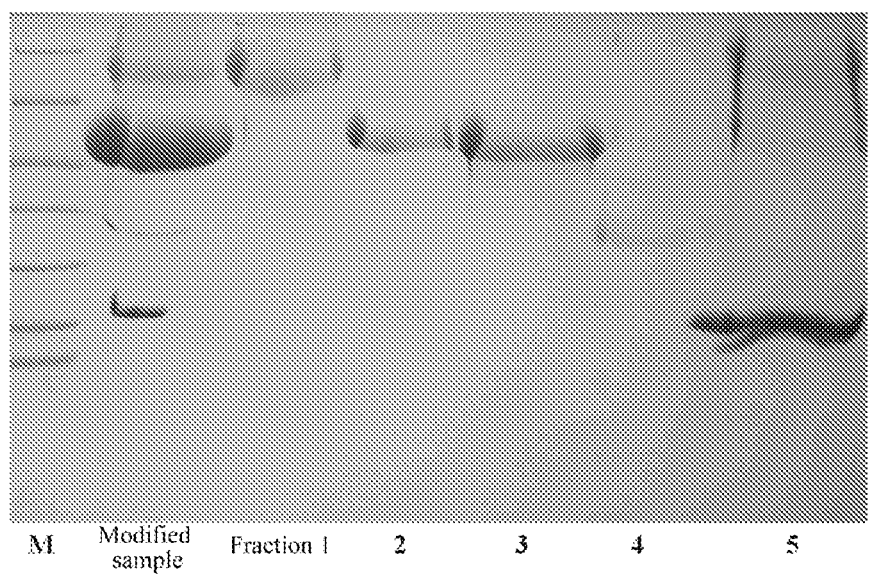
FIG. 2: the result of SDS-PAGE electrophoresis analysis of the modified sample in which endostatin K1 analogue is single-modified with 20 kDa mPEG-ALD at N-terminus, and of the subsequent samples after chromatographic purification. Lane 1 represents low molecular weight standards of 116, 66, 45, 30, 25, 18.4, 14.4 kDa from top to bottom; Lane 2 represents the sample in which endostatin K1 analogue is modified with 20 kDa mPEG-ALD; Lanes 3~7 represent Fractions 1, 2, 3, 4 and 5 obtained by elution with 100, 150, 150, 350 and 500 mM NaCl in chromatographic purification, respectively, wherein 150 mM NaCl eluted fractions (Fractions 2, 3) of Lanes 4, 5 are endostatin K1 analogues single-modified with 20 kDa PEG at N-terminus.

Example 3: Coupling of 20 kDa PEG to Endostatin K1 Analogue at N-Terminal Amino Group Endostatin K1 analogue was dialyzed into a 30 mM sodium acetate solution (pH 5.0±1.0), the protein concentration was determined, and the protein concentration was adjusted to between 5 and 15 mg/ml. The amount of 20 kDa monomethoxy polyethylene glycol propionaldehyde (mPEG-ALD) to be added was calculated according to a molar ratio of the protein of interest to PEG of 1:3, and the amount of the reducing agent sodium cyanoborohydride was calculated according to the volume of the final solution, at a concentration of 20 mM. The desired monomethoxy polyethylene glycol propionaldehyde (mPEG-ALD) and sodium cyanoborohydride were weighed, added to the protein of interest, stirred homogeneously and then allowed to stand at room temperature for 6-8 hours. The electrophoresis graph of the modification result was shown in FIG. 2. Each band in the electrophoresis gel was subjected to content analysis by 1 D gel quantification software Quantity One of Bio-Rad and was compared with molecular weight standards. The result showed that the percentage of single-modified endostatin K1 analogue was above 60%, i.e., an endostatin K1 analogue was modified with a monomethoxy PEG molecule having a molecular weight of 20 kDa.

Example 4: Purification of the Product of Coupling 20 kDa PEG to Endostatin K1 Analogue at N-Terminal Amino Group The solution of product of the coupling reaction between monomethoxy polyethylene glycol propionaldehyde (mPEG-ALD) and endostatin K1 analogue in Example 3 was purified by a cation chromatographic column. SPFF medium (GE Healthcare) was selected, the pH of the reaction solution was adjusted to 5.0~7.0, the cation column was equilibrated with 20 mM $NaH_2PO_4$ (pH adjusted to 5.0~7.0) and the sample was loaded. Gradient elution was carried out using 20 mM $NaH_2PO_4$, 500 mM NaCl (pH 5.0~7.0), and different fractions were collected according to ultraviolet absorptions at 280 nm. The SDS-PAGE analysis was carried out, and the analysis result was shown in FIG. 2. As seen from FIG. 2, Fractions 2 and 3 were the products resulted from single-modification of endostatin K1 analogue with 20 kDa PEG. Based on the same modification principle analysis in Example 2, the single-modification product could be considered as an N-terminal single-modification product.

Figure 3:
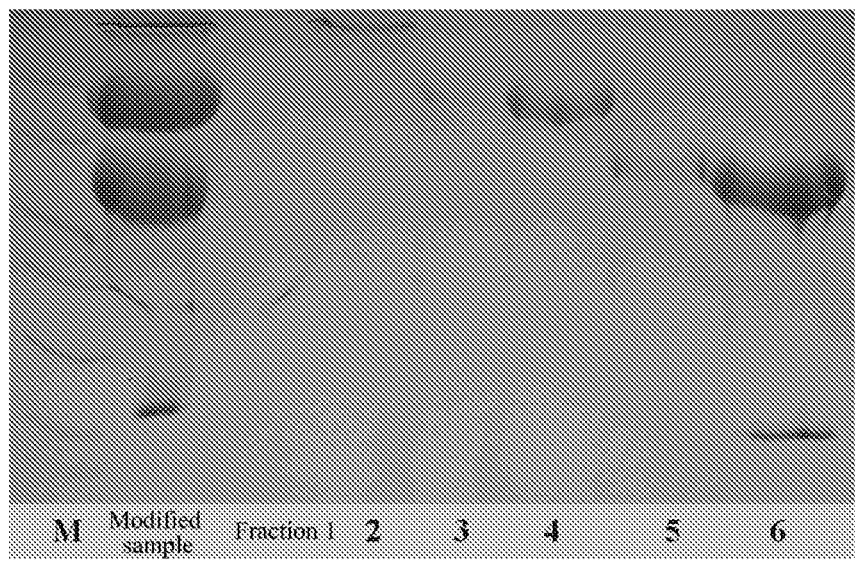
FIG. 3: the result of SDS-PAGE electrophoresis analysis of the modified sample in which endostatin K1 analogue is dual-modified with 20 kDa mPEG-SPA at lysine side-chain amino group and N-terminal amino group, and of the purified samples. Lane 1 represents low molecular weight standards of 116, 66, 45, 30, 25, 18.4, 14.4 kDa from top to bottom; Lane 2 represents the sample in which endostatin is modified with 20 kDa mPEG-SPA; Lanes 3~8 represent Fractions 1, 2, 3, 4, 5 and 6 obtained by elution with 25, 50, 75, 100, 200 and 500 mM NaCl in chromatographic purification, respectively, wherein 100 mM NaCl eluted fraction (Fraction 4) of Lane 6 is the fraction of a product in which K1 analogue is dual-modified.

Example 5: Dual-Coupling of 20 kDa PEG to Endostatin K1 Analogue at Lysine Side-Chain Amino Group and N-Terminal Amino Group Endostatin K1 analogue was dialyzed into a 20 mM $NaH_2PO_4$ solution (pH 8.5), the protein concentration was determined, and the protein concentration was adjusted to between 5 and 15 mg/ml. The amount of 20 kDa monomethoxy polyethylene glycol succinimidyl propionate to be added was calculated according to a molar ratio of the protein of interest to PEG of 1:10. The monomethoxy polyethylene glycol succinimidyl propionate was added to the protein of interest, stirred homogeneously and then allowed to stand at room temperature for 60-120 min. The electrophoresis graph of the modification result was shown in FIG. 3. Each band in the electrophoresis gel was subjected to content analysis by 1 D gel quantification software Quantity One of Bio-Rad and was compared with molecular weight standards. The percentage of dual-modified endostatin K1 analogue (with a molecular weight of 60 kDa) was above 50%, i.e., an endostatin K1 analogue was modified with two monomethoxy PEG molecules having a molecular weight of 20 kDa.

Example 6: Purification of the Product of Dual-Coupling 20 kDa PEG to Endostatin K1 Analogue at Lysine Side-Chain Amino Group and N-Terminal Amino Group The solution of the product of the coupling reaction between monomethoxy polyethylene glycol succinimidyl propionate and endostatin K1 analogue in Example 5 was purified by a cation chromatographic column. SPFF medium (GE Healthcare) was selected, the pH of the reaction solution was adjusted to 5.0~7.0, the cation column was equilibrated with 20 mM $NaH_2PO_4$ (pH adjusted to 5.0~7.0) and the sample was loaded. Gradient elution was carried out using 20 mM $NaH_2PO_4$, 500 mM NaCl (pH 5.0~7.0), and different fractions were collected according to ultraviolet absorptions at 280 nm. The SDS-PAGE analysis was carried out, and the analysis result was shown in FIG. 3. As seen from FIG. 3, Fraction 4 was a product resulted from dual-modification of endostatin K1 analogue with 20 kDa polyethylene glycol.

Example 7: Coupling of 20 kDa PEG to Endostatin K2 Analogue at N-Terminal Amino Group, and Purification N-terminal coupling was carried out by the method as described in Example 3, the modification product was purified by the method as described in Example 4, and similar experimental result was obtained.

Example 8: Coupling of 20 kDa PEG to Endostatin K2 Analogue at Lysine Side-Chain Amino Group and N-Terminal Amino Group, and Purification Coupling was carried out by the method as described in Example 5, the modification product was purified by the method as described in Example 6, and similar experimental result was obtained.

Example 9: Coupling of 20 kDa PEG to Endostatin K3 Analogue at N-Terminal Amino Group, and Purification N-terminal coupling was carried out by the method as described in Example 3, the modification product was purified by the method as described in Example 4, and similar experimental result was obtained.

Example 10: Coupling of 20 kDa PEG to Endostatin K3 Analogue at Lysine Side-Chain Amino Group and N-Terminal Amino Group, and Purification Coupling was carried out by the method as described in Example 5, the modification product was purified by the method as described in Example 6, and similar experimental result was obtained.

Example 11: Coupling of 20 kDa PEG to Endostatin K4 Analogue at N-Terminal Amino Group, and Purification N-terminal coupling was carried out by the method as described in Example 3, the modification product was purified by the method as described in Example 4, and similar experimental result was obtained.

Example 12: Coupling of 20 kDa PEG to Endostatin K4 Analogue at Lysine Side-Chain Amino Group and N-Terminal Amino Group, and Purification N-terminal coupling was carried out by the method as described in Example 5, the modification product was purified by the method as described in Example 6, and similar experimental result was obtained.

Example 13: Coupling of 20 kDa PEG to Endostatin ESC Analogue

Figure 4:
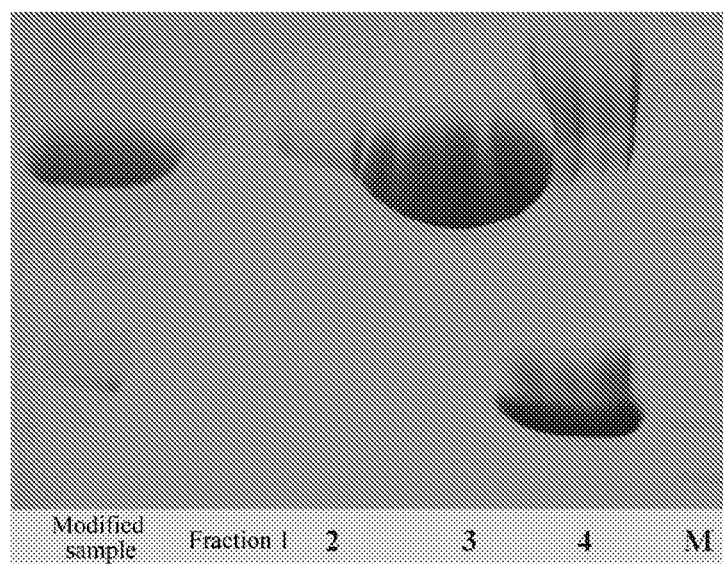
FIG. 4: the result of SDS-PAGE electrophoresis analysis of the modified sample in which endostatin ESC analogue is modified with 20 kDa mPEG-MAL at a thiol group, and of the subsequent samples after chromatographic purification. Lane 1 represents the sample in which endostatin ESC analogue is modified with 20 kDa mPEG-MAL; Lanes 2~5 represent the fractions obtained by elution with 100, 150, 200 and 500 mM NaCl in chromatographic purification; Lane 6 represents low molecular weight standards of 116, 66, 45, 30, 25, 18.4, 14.4 kDa from top to bottom; wherein 200 mM NaCl eluted fraction (Fraction 3) of Lane 4 is the fraction of a product in which ESC analogue is single-modified at a thiol group.

Endostatin ESC analogue was dialyzed into a 20 mM $NaH_2PO_4$ solution (pH 7.5), the protein concentration was determined, and the protein concentration was adjusted to between 5 and 15 mg/ml. The amount of 20 kDa monomethoxy polyethylene glycol maleimide (mPEG-MAL) to be added was calculated according to a molar ratio of the protein of interest to PEG of 1:5. mPEG-MAL was added to the protein of interest, stirred homogeneously and then allowed to stand at room temperature for 6-8 hours. The electrophoresis graph of the modification result was shown in FIG. 4. Each band in the electrophoresis gel was subjected to content analysis by 1 D gel quantification software Quantity One of Bio-Rad and was compared with molecular weight standards. The percentage of single-modified endostatin ESC analogue (with a molecular weight of 40 kDa) was above 80%, i.e., an endostatin K1 analogue was modified with one mPEG-MAL molecule having a molecular weight of 20 kDa. Since mPEG-MAL can only react with free thiol group, the PEG modification site of this product can be considered as the free thiol group of endostatin ESC analogue.

Example 14: Purification of the Product of Coupling of 20 kDa PEG to Endostatin ESC Analogue The solution of the product of the coupling reaction between monomethoxy polyethylene glycol maleimide (mPEG-MAL) and endostatin KSC analogue in Example 13 was purified by a cation chromatographic column. SPFF medium (GE Healthcare) was selected, the pH of the reaction solution was adjusted to 5.0~7.0, the cation column was equilibrated with 20 mM $NaH_2PO_4$ (pH adjusted to 5.0~7.0) and the sample was loaded. Gradient elution was carried out using 20 mM $NaH_2PO_4$, 500 mM NaCl (pH 5.0~7.0), and different fractions were collected according to ultraviolet absorptions at 280 nm. The SDS-PAGE analysis was carried out, and the analysis result was shown in FIG. 4. As seen from FIG. 4, Fraction 3 was a product resulted from single-modification of endostatin ESC analogue with 20 kDa PEG.

Example 15: Coupling of 20 kDa PEG to Endostatin NK1, NK2, NK3, NK4, ESK, NESK Analogues at N-Terminal Amino Group, and Purification N-terminal coupling was carried out by the method as described in Example 3, the modification product was purified by the method as described in Example 4, and similar experimental result was obtained.

Example 16: Coupling of 20 kDa PEG to Endostatin NK1, NK2, NK3, NK4, ESK, NESK Analogues at Lysine Side-Chain Amino Group and N-Terminal Amino Group, and Purification Coupling was carried out by the method as described in Example 5, the modification product was purified by the method as described in Example 6, and similar experimental result was obtained.

Figure 5:
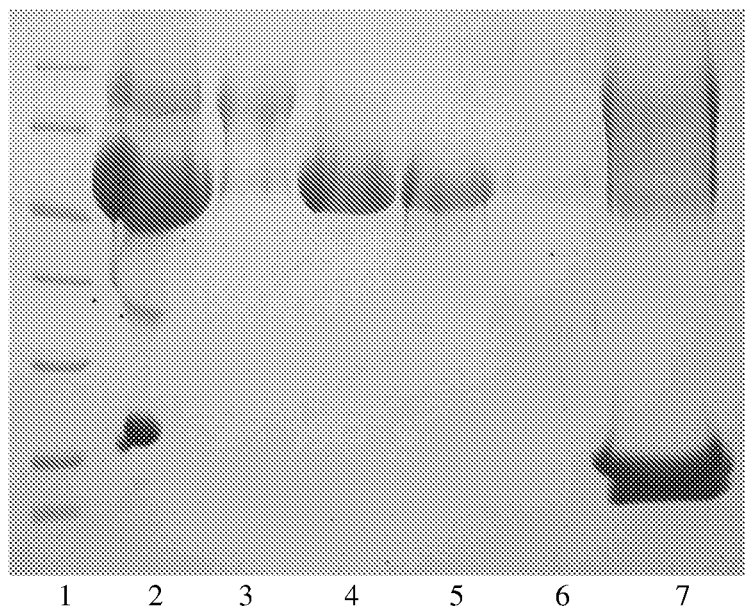
FIG. 5: the result of SDS-PAGE electrophoresis analysis of the modified sample in which endostatin K1 analogue is modified with 20 kDa mPEG-ALD at lysine side-chain amino group, and of the subsequent samples after chromatographic purification. Lane 1 represents low molecular weight standards of 116, 66, 45, 30, 25, 18.4, 14.4 kDa from top to bottom; Lane 2 represents the sample in which endostatin is modified with 20 kDa mPEG-ALD; Lanes 3~7 represent the fractions obtained by elution with 50, 100, 125, 200 and 500 mM NaCl in chromatographic purification, wherein Lanes 4, 5 represent endostatin analogues single-modified with 20 kDa PEG, and it is confirmed by analyzing the modification sites of the two samples that the sample of Lane 4 is a product resulted from single modification with PEG at N-terminus and a little amount of a product resulted from single modification at lysine side-chain amino group, and the sample of Lane 5 is a product in which endostatin K1 analogue is single-modified at lysine side-chain amino group.

Example 17: Purification of the Product of Coupling of 20 kDa PEG to Endostatin K1 Analogue at Lysine Side-Chain Amino Group Endostatin K1 analogue was dialyzed into a 20 mM $NaH_2PO_4$ solution (pH 8.5±0.5), the protein concentration was determined, and the protein concentration was adjusted to between 10 and 20 mg/ml. The amount of 20 kDa monomethoxy polyethylene glycol propionaldehyde (mPEG-ALD) to be added was calculated according to a molar ratio of the protein of interest to PEG of 1:1, and the amount of the reducing agent sodium cyanoborohydride was calculated according to the volume of the final solution, at a concentration of 10 mM. The desired monomethoxy polyethylene glycol propionaldehyde (mPEG-ALD) and sodium cyanoborohydride were weighed, added to the protein of interest, stirred homogeneously and then allowed to stand at room temperature for 6-8 hours. The solution of the reaction product was purified by a cation chromatographic column. Macrocap SP medium (GE Healthcare) was particularly selected, and the pH of the reaction solution was adjusted to 4.5±0.5. The cation column was equilibrated with 30 mM NaAc (pH adjusted to 4.0~5.0) and the sample was loaded. Gradient elution was carried out using 30 mM NaAc, 500 mM NaCl (pH 4.0~5.0), and different fractions were collected according to ultraviolet absorptions at 280 nm. The modification sample and the fractions collected after subsequent purification were analyzed by SDS-PAGE electrophoresis, and the analysis result obtained was shown in FIG. 5. The two single-modified fractions as collected, i.e., the samples of Lanes 4 and 5, were digested by trypsin and then were analyzed for their modification sites by mass spectrometry. It was confirmed that the fraction in the sample of Lane 5 was a single-modification product at lysine side-chain amino group.

Example 18: Coupling of 20 kDa PEG to Endostatin K2, K3, NK1, NK2, NK3 Analogues at Lysine Side-Chain Amino Group, and Purification Coupling and purification of the modification product were carried out by the method as described in Example 17, and similar experimental result was obtained.

Example 19: Activity Assay on Modification Products

Cell viability assays were performed on all the purified products of interest obtained in Example 1 to Example 18, and the optimal modification protocol was selected from them. HMECs were selected, the Migration (Tranwell Assay) assay was used, and the number of cells was counted to reflect protein activity (see Luo yongzhang et al., Endostatin inhibits tumourlymphangiogenesis and lymphatic metastasis via cell surface nucleolin on lymphangiogenic endothelial cells (J Pathol 2010; 222: 249-260), the modification products were analyzed for their inhibition rate for HMEC migration, and the result was shown in Table 1:

TABLE 1

Result on the inhibition rate of modification products for HMEC migration

| Sample name for activity assay | Inhibition rate (%) |
|---|---|
| naturally occurring human endostatin | 21.5 |
| single-modification product of naturally occurring human endostatin at N-terminal amino group | 61.3 |
| single-modification product of endostatin K1 analogue at N-terminal amino group | 32.3 |
| single-modification product of endostatin K1 analogue at lysine side-chain amino group | 39.8 |
| dual-modification product of endostatin K1 analogue at lysine side-chain amino group and N-terminal amino group | 41.9 |
| single-modification product of endostatin K2 analogue at N-terminal amino group | 48.9 |
| single-modification product of endostatin K2 analogue at lysine side-chain amino group | 74.2 |
| dual-modification product of endostatin K2 analogue at lysine side-chain amino group and N-terminal amino group | 79.0 |
| single-modification product of endostatin K3 analogue at N-terminal amino group | 31.7 |
| single-modification product of endostatin K3 analogue at lysine side-chain amino group | 23.2 |
| dual-modification product of endostatin K3 analogue at lysine side-chain amino group and N-terminal amino group | 7.0 |
| single-modification product of at endostatin K4 analogue at N-terminal amino group | 15.0 |
| dual-modification product of endostatin K4 analogue at lysine side-chain amino group and N-terminal amino group | 5.0 |
| coupling product of endostatin ESC analogue at C-terminal thiol group | 42.0 |
| single-modification product of endostatin NK1 analogue at N-terminal amino group | 30.0 |
| single-modification product of endostatin NK1 analogue at lysine side-chain amino group | 37.2 |
| dual-modification product of endostatin NK1 analogue at lysine side-chain amino group and N-terminal amino group | 38.2 |
| single-modification product of endostatin NK2 analogue at N-terminal amino group | 44.5 |
| single-modification product of endostatin NK2 analogue at lysine side-chain amino group | 72.1 |
| dual-modification product of endostatin NK2 analogue at lysine side-chain amino group and N-terminal amino group | 75.0 |
| single-modification product of endostatin NK3 analogue at N-terminal amino group | 27.9 |
| single-modification product of endostatin NK3 analogue at lysine side-chain amino group | 20.2 |
| dual-modification product of endostatin NK3 analogue at lysine side-chain amino group and N-terminal amino group | 5.4 |
| single-modification product of endostatin NK4 analogue at N-terminal amino group | 12.0 |
| dual-modification product of endostatin NK4 analogue at lysine side-chain amino group and N-terminal amino group | 3.6 |
| single-modification product of endostatin ESK analogue at N-terminal amino group | 32.0 |
| dual-modification product of endostatin ESK analogue at lysine side-chain amino group and N-terminal amino group | 56.0 |
| single-modification product of endostatin NESK analogue at N-terminal amino group | 29.3 |
| dual-modification product of endostatin NESK analogue at lysine side-chain amino group and N-terminal amino group | 50.4 |

As shown in the activity result above, the N-terminal single-modification products of all the analogues had an inhibition rate for HMEC migration lower than that of N-terminal single-modification product of endostatin, indicating that mutations had certain effects on protein activity; the result of single-modification at lysine side-chain amino group showed that the single-modification product at the second lysine side-chain amino group (i.e. endostatin K2 analogue) had the highest inhibition rate for HMEC migration, even higher than that of N-terminal single-modification product of endostatin; among the dual-modification products at N-terminal amino group and lysine side-chain amino group, the dual-modification product at the second lysine side-chain amino group and N-terminal amino group (i.e., endostatin K2 analogue) had the highest inhibition rate for HMEC migration among all the products.

The tertiary structure of endostatin molecule (FIG. 6) was taken into consideration for comprehensive analysis. Endostatin molecule has 6 amino groups that can be modified by PEG, i.e., N-terminal amino group and 5 lysine side-chain amino groups. Among them, the fifth lysine residue is located at C-terminus, close to N-terminus. It is difficult to achieve single modification at the fifth lysine side-chain amino group due to steric hindrance. The preparation difficulty can be reduced through thiol modification by adding a cysteine residue after the fifth lysine. Among said six sites for modification, the second lysine residue is farthest away from nucleolin binding domain of the protein, and N-terminus is farther away from nucleolin binding domain of the protein. When PEG modification is performed, the ethylene glycol long chain has the least influence on the binding domain, and thus when single-modified or dual modified at N-terminal amino group and the second lysine side-chain amino group, the products are superior to the modification protocols at other sites in terms of inhibition rate for HMEC migration. This sufficiently indicated that it was an optimal choice for endostatin to modify it at a site distant from nucleolin binding domain.

In order to confirm the conclusion, according to the tertiary structural characteristic of endostatin molecule, a lysine residue (i.e., endostatin ESK analogue) at position 127 on the surface of the tertiary structure, which was distant from both the nucleolin binding domain and the second lysine residue, was introduced for modification, and the result showed that the dual-modification product of the analogue had an inhibition rate for HMEC migration lower than that of endostatin K2 analogue, indicating that dual modification of endostatin K2 analogue was an optimal choice for endostatin or analogues thereof.

Figure 6:
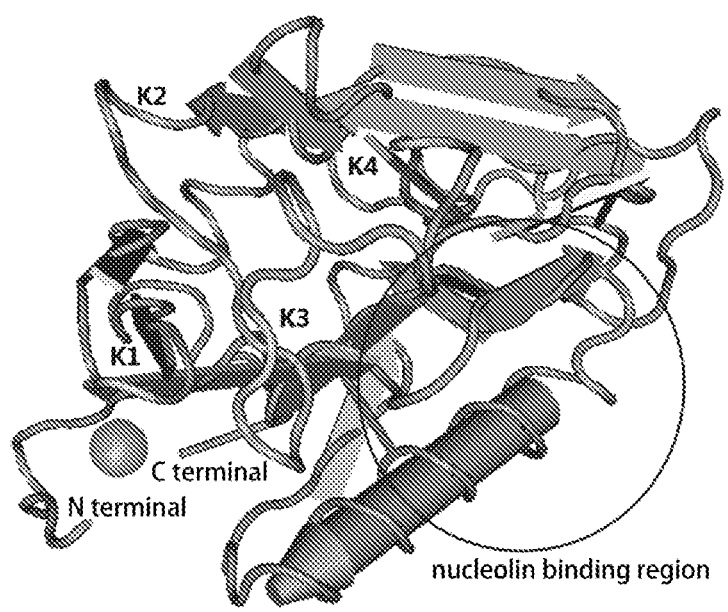
FIG. 6: the tertiary structure graph of human endostatin, in which N-terminus, C-terminus and lysine residue K1 at position 76, lysine residue K2 at position 96, lysine residue K3 at position 107, lysine residue K4 at position 118 of human endostatin protein, as well as the binding domain of the protein to the receptor Nucleolin, are indicated.
Figure 7:
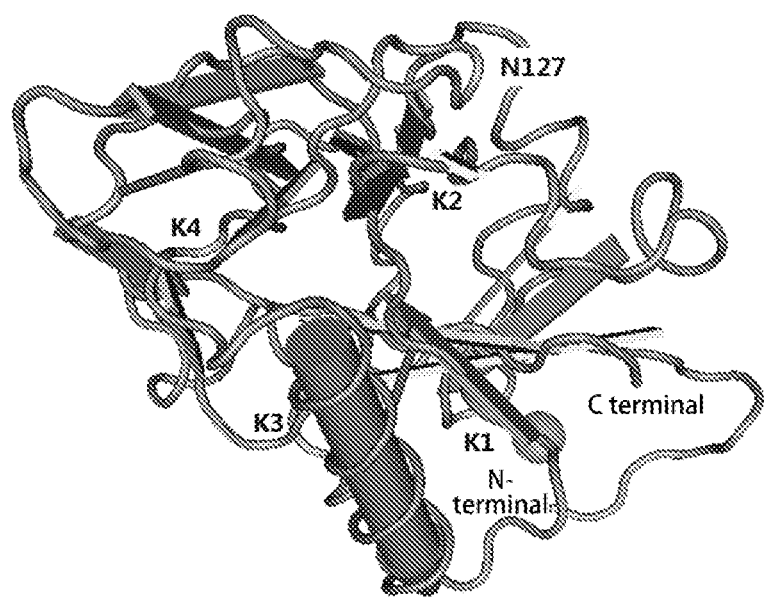
FIG. 7: the tertiary structure graph of human endostatin, in which N-terminus, C-terminus, lysine residue K1 at position 76, lysine residue K2 at position 96, lysine residue K3 at position 107, lysine residue K4 at position 118, and asparagine residue at position 127 of human endostatin protein, are indicated.

As shown in FIG. 6 and FIG. 7, PEG modification at different regions on the surface of ES molecule had different effects on protein activity. N-terminal single-modified and K2 single-modification products had the activity of inhibiting HMEC migration (i.e., inhibition rate) increased significantly, and the dual-modification product at the two sites had the activity of inhibiting HMEC migration (i.e., inhibition rate) increased most significantly. K2 was farthest away from nucleolin binding domain, and single modification led to the greatest increase in the activity of protein to inhibit HMEC migration, while the K1, K3, K4 and C-terminal modification products had the activity of protein to inhibit HMEC migration enhanced little or reduced. Moreover, for dual-modification products, similar results were obtained, indicating that K2 distant from nucleolin binding domain was an optimal choice for modification. In order to further prolong the half-life of products, dual modification at N-terminus and K2 was an optimal choice. In order to confirm whether there was an insertable modification site similar to K2 in a region within the K2 region andaway from K3, K4 region, a site mutation was performed at N127 of ES natural structure to form a new modification site, and relevant experiments were performed. The result demonstrated that the modification products at this region (no matter single-modification product at this region or dual-modification product at this region and N-terminus) increased the activity of inhibiting HMEC migration to an extent less than that of the corresponding modification products at K2. These sufficiently indicated that dual-modification at K2 and N-terminus was an optimal choice for enhancing protein activity and prolonging half-life.

SEQUENCE LISTING

```
<160> NUMBER OF SEQ ID NOS: 15

<210> SEQ ID NO 1
<211> LENGTH: 184
<212> TYPE: PRT
<213> ORGANISM: Homo sapiens

<400> SEQUENCE: 1

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asn Gly Lys Asp Val Leu Thr His
            100                 105                 110

Pro Thr Trp Pro Gln Lys Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Tyr Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys
            180
```

```
<210> SEQ ID NO 2
<211> LENGTH: 184
<212> TYPE: PRT
<213> ORGANISM: Homo sapiens
<220> FEATURE:
<221> NAME/KEY: MISC_FEATURE
<222> LOCATION: (96)..(96)
<223> OTHER INFORMATION: X2 may be any naturally occurring amino acid
      other than lysine
<220> FEATURE:
<221> NAME/KEY: MISC_FEATURE
<222> LOCATION: (107)..(107)
<223> OTHER INFORMATION: X3 may be any naturally occurring amino acid
      other than lysine
<220> FEATURE:
<221> NAME/KEY: MISC_FEATURE
<222> LOCATION: (118)..(118)
<223> OTHER INFORMATION: X4 may be any naturally occurring amino acid
      other than lysine
<220> FEATURE:
<221> NAME/KEY: MISC_FEATURE
<222> LOCATION: (184)..(184)
<223> OTHER INFORMATION: X5 may be any naturally occurring amino acid
      other than lysine

<400> SEQUENCE: 2

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Gly Pro Leu Xaa
                85                  90                  95

Pro Gly Ala Arg Ile Phe Ser Phe Asn Gly Xaa Asp Val Leu Thr His
            100                 105                 110

Pro Thr Trp Pro Gln Xaa Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Tyr Ser Leu Leu Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Xaa
            180

<210> SEQ ID NO 3
<211> LENGTH: 184
<212> TYPE: PRT
<213> ORGANISM: Homo sapiens
<220> FEATURE:
<221> NAME/KEY: MISC_FEATURE
<222> LOCATION: (76)..(76)
<223> OTHER INFORMATION: X1 may be any naturally occurring amino acid
      other than lysine
<220> FEATURE:
<221> NAME/KEY: MISC_FEATURE
<222> LOCATION: (107)..(107)
<223> OTHER INFORMATION: X3 may be any naturally occurring amino acid
      other than lysine
```

-continued

```
<220> FEATURE:
<221> NAME/KEY: MISC_FEATURE
<222> LOCATION: (118)..(118)
<223> OTHER INFORMATION: X4 may be any naturally occurring amino acid
      other than lysine
<220> FEATURE:
<221> NAME/KEY: MISC_FEATURE
<222> LOCATION: (184)..(184)
<223> OTHER INFORMATION: X5 may be any naturally occurring amino acid
      other than lysine

<400> SEQUENCE: 3

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
    50                  55                  60

Ala Asp Arg Ala Ala Val Pro Ile Val Asn Leu Xaa Asp Glu Leu Leu
65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asn Gly Xaa Asp Val Leu Thr His
            100                 105                 110

Pro Thr Trp Pro Gln Xaa Ser Val Trp His Gly Ser Asp Pro Asn Gly
        115                 120                 125

Arg Arg Leu Thr Glu Ser Tyr Cys Glu Thr Trp Arg Thr Glu Ala Pro
    130                 135                 140

Ser Ala Thr Gly Gln Ala Tyr Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Xaa
            180

<210> SEQ ID NO 4
<211> LENGTH: 184
<212> TYPE: PRT
<213> ORGANISM: Homo sapiens
<220> FEATURE:
<221> NAME/KEY: MISC_FEATURE
<222> LOCATION: (76)..(76)
<223> OTHER INFORMATION: X1 may be any naturally occurring amino acid
      other than lysine
<220> FEATURE:
<221> NAME/KEY: MISC_FEATURE
<222> LOCATION: (96)..(96)
<223> OTHER INFORMATION: X2 may be any naturally occurring amino acid
      other than lysine
<220> FEATURE:
<221> NAME/KEY: MISC_FEATURE
<222> LOCATION: (118)..(118)
<223> OTHER INFORMATION: X4 may be any naturally occurring amino acid
      other than lysine
<220> FEATURE:
<221> NAME/KEY: MISC_FEATURE
<222> LOCATION: (184)..(184)
<223> OTHER INFORMATION: X5 may be any naturally occurring amino acid
      other than lysine

<400> SEQUENCE: 4

Met His Ser His Arg Asp Phe Gln Pro Val Leu His Leu Val Ala Leu
1               5                   10                  15
```

```
Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
 50                  55                  60

Ala Asp Arg Ala Ala Val Pro Ile Val Asn Leu Xaa Asp Glu Leu Leu
 65                  70                  75                  80

Phe Pro Ser Trp Glu Ala Leu Phe Ser Gly Ser Glu Gly Pro Leu Xaa
                85                  90                  95

Pro Gly Ala Arg Ile Phe Ser Phe Asn Gly Lys Asp Val Leu Thr His
            100                 105                 110

Pro Thr Trp Pro Gln Xaa Ser Val Trp His Gly Ser Asp Pro Asn Gly
            115                 120                 125

Arg Arg Leu Thr Glu Ser Tyr Cys Glu Thr Trp Arg Thr Glu Ala Pro
130                 135                 140

Ser Ala Thr Gly Gln Ala Tyr Ser Leu Leu Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Xaa
            180
```

<210> SEQ ID NO 5
<211> LENGTH: 184
<212> TYPE: PRT
<213> ORGANISM: Homo sapiens
<220> FEATURE:
<221> NAME/KEY: MISC_FEATURE
<222> LOCATION: (76)..(76)
<223> OTHER INFORMATION: X1 may be any naturally occurring amino acid other than lysine
<220> FEATURE:
<221> NAME/KEY: MISC_FEATURE
<222> LOCATION: (96)..(96)
<223> OTHER INFORMATION: X2 may be any naturally occurring amino acid other than lysine
<220> FEATURE:
<221> NAME/KEY: MISC_FEATURE
<222> LOCATION: (107)..(107)
<223> OTHER INFORMATION: X3 may be any naturally occurring amino acid other than lysine
<220> FEATURE:
<221> NAME/KEY: MISC_FEATURE
<222> LOCATION: (184)..(184)
<223> OTHER INFORMATION: X5 may be any naturally occurring amino acid other than lysine

<400> SEQUENCE: 5

```
Met His Ser His Arg Asp Phe Gln Pro Val Leu His Leu Val Ala Leu
 1               5                  10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
 50                  55                  60

Ala Asp Arg Ala Ala Val Pro Ile Val Asn Leu Xaa Asp Glu Leu Leu
 65                  70                  75                  80

Phe Pro Ser Trp Glu Ala Leu Phe Ser Gly Ser Glu Gly Pro Leu Xaa
                85                  90                  95
```

```
Pro Gly Ala Arg Ile Phe Ser Phe Asn Gly Xaa Asp Val Leu Thr His
                100                 105                 110

Pro Thr Trp Pro Gln Lys Ser Val Trp His Gly Ser Asp Pro Asn Gly
            115                 120                 125

Arg Arg Leu Thr Glu Ser Tyr Cys Glu Thr Trp Arg Thr Glu Ala Pro
        130                 135                 140

Ser Ala Thr Gly Gln Ala Tyr Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Xaa
            180

<210> SEQ ID NO 6
<211> LENGTH: 185
<212> TYPE: PRT
<213> ORGANISM: Homo sapiens

<400> SEQUENCE: 6

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Lys Asp Glu Leu Leu
65                  70                  75                  80

Phe Pro Ser Trp Glu Ala Leu Phe Ser Gly Ser Glu Gly Pro Leu Lys
                85                  90                  95

Pro Gly Ala Arg Ile Phe Ser Phe Asn Gly Lys Asp Val Leu Thr His
                100                 105                 110

Pro Thr Trp Pro Gln Lys Ser Val Trp His Gly Ser Asp Pro Asn Gly
            115                 120                 125

Arg Arg Leu Thr Glu Ser Tyr Cys Glu Thr Trp Arg Thr Glu Ala Pro
        130                 135                 140

Ser Ala Thr Gly Gln Ala Tyr Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Lys Cys
            180                 185

<210> SEQ ID NO 7
<211> LENGTH: 192
<212> TYPE: PRT
<213> ORGANISM: Homo sapiens
<220> FEATURE:
<221> NAME/KEY: MISC_FEATURE
<222> LOCATION: (104)..(104)
<223> OTHER INFORMATION: X2 may be any naturally occurring amino acid
      other than lysine
<220> FEATURE:
<221> NAME/KEY: MISC_FEATURE
<222> LOCATION: (115)..(115)
<223> OTHER INFORMATION: X3 may be any naturally occurring amino acid
      other than lysine
<220> FEATURE:
```

<221> NAME/KEY: MISC_FEATURE
<222> LOCATION: (126)..(126)
<223> OTHER INFORMATION: X4 may be any naturally occurring amino acid
      other than lysine
<220> FEATURE:
<221> NAME/KEY: MISC_FEATURE
<222> LOCATION: (192)..(192)
<223> OTHER INFORMATION: X5 may be any naturally occurring amino acid
      other than lysine

<400> SEQUENCE: 7

Met Gly Gly Ser His His His His His His Ser His Arg Asp Phe Gln
1               5                   10                  15

Pro Val Leu His Leu Val Ala Leu Asn Ser Pro Leu Ser Gly Gly Met
                20                  25                  30

Arg Gly Ile Arg Gly Ala Asp Phe Gln Cys Phe Gln Gln Ala Arg Ala
            35                  40                  45

Val Gly Leu Ala Gly Thr Phe Arg Ala Phe Leu Ser Ser Arg Leu Gln
    50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Ser Glu Gly Pro Leu Xaa Pro Gly Ala Arg Ile Phe Ser Phe
                100                 105                 110

Asn Gly Xaa Asp Val Leu Thr His Pro Thr Trp Pro Gln Xaa Ser Val
            115                 120                 125

Trp His Gly Ser Asp Pro Asn Gly Arg Arg Leu Thr Glu Ser Tyr Cys
    130                 135                 140

Glu Thr Trp Arg Thr Glu Ala Pro Ser Ala Thr Gly Gln Ala Tyr Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Xaa
            180                 185                 190

<210> SEQ ID NO 8
<211> LENGTH: 192
<212> TYPE: PRT
<213> ORGANISM: Homo sapiens
<220> FEATURE:
<221> NAME/KEY: MISC_FEATURE
<222> LOCATION: (84)..(84)
<223> OTHER INFORMATION: X1 may be any naturally occurring amino acid
      other than lysine
<220> FEATURE:
<221> NAME/KEY: MISC_FEATURE
<222> LOCATION: (115)..(115)
<223> OTHER INFORMATION: X3 may be any naturally occurring amino acid
      other than lysine
<220> FEATURE:
<221> NAME/KEY: MISC_FEATURE
<222> LOCATION: (126)..(126)
<223> OTHER INFORMATION: X4 may be any naturally occurring amino acid
      other than lysine
<220> FEATURE:
<221> NAME/KEY: MISC_FEATURE
<222> LOCATION: (192)..(192)
<223> OTHER INFORMATION: X5 may be any naturally occurring amino acid
      other than lysine

<400> SEQUENCE: 8

Met Gly Gly Ser His His His His His His Ser His Arg Asp Phe Gln
1               5                   10                  15

-continued

```
Pro Val Leu His Leu Val Ala Leu Asn Ser Pro Leu Ser Gly Gly Met
             20                  25                  30

Arg Gly Ile Arg Gly Ala Asp Phe Gln Cys Phe Gln Gln Ala Arg Ala
         35                  40                  45

Val Gly Leu Ala Gly Thr Phe Arg Ala Phe Leu Ser Ser Arg Leu Gln
     50                  55                  60

Asp Leu Tyr Ser Ile Val Arg Arg Ala Asp Arg Ala Ala Val Pro Ile
 65                  70                  75                  80

Val Asn Leu Xaa Asp Glu Leu Leu Phe Pro Ser Trp Glu Ala Leu Phe
                 85                  90                  95

Ser Gly Ser Glu Gly Pro Leu Lys Pro Gly Ala Arg Ile Phe Ser Phe
            100                 105                 110

Asn Gly Xaa Asp Val Leu Thr His Pro Thr Trp Pro Gln Xaa Ser Val
        115                 120                 125

Trp His Gly Ser Asp Pro Asn Gly Arg Arg Leu Thr Glu Ser Tyr Cys
    130                 135                 140

Glu Thr Trp Arg Thr Glu Ala Pro Ser Ala Thr Gly Gln Ala Tyr Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Xaa
            180                 185                 190
```

<210> SEQ ID NO 9
<211> LENGTH: 192
<212> TYPE: PRT
<213> ORGANISM: Homo sapiens
<220> FEATURE:
<221> NAME/KEY: MISC_FEATURE
<222> LOCATION: (84)..(84)
<223> OTHER INFORMATION: X1 may be any naturally occurring amino acid
      other than lysine
<220> FEATURE:
<221> NAME/KEY: MISC_FEATURE
<222> LOCATION: (104)..(104)
<223> OTHER INFORMATION: X2 may be any naturally occurring amino acid
      other than lysine
<220> FEATURE:
<221> NAME/KEY: MISC_FEATURE
<222> LOCATION: (126)..(126)
<223> OTHER INFORMATION: X4 may be any naturally occurring amino acid
      other than lysine
<220> FEATURE:
<221> NAME/KEY: MISC_FEATURE
<222> LOCATION: (192)..(192)
<223> OTHER INFORMATION: X5 may be any naturally occurring amino acid
      other than lysine

<400> SEQUENCE: 9

```
Met Gly Gly Ser His His His His His Ser His Arg Asp Phe Gln
  1               5                  10                  15

Pro Val Leu His Leu Val Ala Leu Asn Ser Pro Leu Ser Gly Gly Met
             20                  25                  30

Arg Gly Ile Arg Gly Ala Asp Phe Gln Cys Phe Gln Gln Ala Arg Ala
         35                  40                  45

Val Gly Leu Ala Gly Thr Phe Arg Ala Phe Leu Ser Ser Arg Leu Gln
     50                  55                  60

Asp Leu Tyr Ser Ile Val Arg Arg Ala Asp Arg Ala Ala Val Pro Ile
 65                  70                  75                  80

Val Asn Leu Xaa Asp Glu Leu Leu Phe Pro Ser Trp Glu Ala Leu Phe
                 85                  90                  95
```

```
Ser Gly Ser Glu Gly Pro Leu Xaa Pro Gly Ala Arg Ile Phe Ser Phe
            100                 105                 110

Asn Gly Lys Asp Val Leu Thr His Pro Thr Trp Pro Gln Xaa Ser Val
        115                 120                 125

Trp His Gly Ser Asp Pro Asn Gly Arg Arg Leu Thr Glu Ser Tyr Cys
    130                 135                 140

Glu Thr Trp Arg Thr Glu Ala Pro Ser Ala Thr Gly Gln Ala Tyr Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Xaa
            180                 185                 190
```

<210> SEQ ID NO 10
<211> LENGTH: 192
<212> TYPE: PRT
<213> ORGANISM: Homo sapiens
<220> FEATURE:
<221> NAME/KEY: MISC_FEATURE
<222> LOCATION: (84)..(84)
<223> OTHER INFORMATION: X1 may be any naturally occurring amino acid
      other than lysine
<220> FEATURE:
<221> NAME/KEY: MISC_FEATURE
<222> LOCATION: (104)..(104)
<223> OTHER INFORMATION: X2 may be any naturally occurring amino acid
      other than lysine
<220> FEATURE:
<221> NAME/KEY: MISC_FEATURE
<222> LOCATION: (115)..(115)
<223> OTHER INFORMATION: X3 may be any naturally occurring amino acid
      other than lysine
<220> FEATURE:
<221> NAME/KEY: MISC_FEATURE
<222> LOCATION: (192)..(192)
<223> OTHER INFORMATION: X5 may be any naturally occurring amino acid
      other than lysine

<400> SEQUENCE: 10

```
Met Gly Gly Ser His His His His Ser His Arg Asp Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala
        35                  40                  45

Val Gly Leu Ala Gly Thr Phe Arg Ala Phe Leu Ser Ser Arg Leu Gln
    50                  55                  60

Asp Leu Tyr Ser Ile Val Arg Arg Ala Asp Arg Ala Ala Val Pro Ile
65                  70                  75                  80

Val Asn Leu Xaa Asp Glu Leu Leu Phe Pro Ser Trp Glu Ala Leu Phe
                85                  90                  95

Ser Gly Ser Glu Gly Pro Leu Xaa Pro Gly Ala Arg Ile Phe Ser Phe
            100                 105                 110

Asn Gly Xaa Asp Val Leu Thr His Pro Thr Trp Pro Gln Lys Ser Val
        115                 120                 125

Trp His Gly Ser Asp Pro Asn Gly Arg Arg Leu Thr Glu Ser Tyr Cys
    130                 135                 140

Glu Thr Trp Arg Thr Glu Ala Pro Ser Ala Thr Gly Gln Ala Tyr Ser
145                 150                 155                 160

Leu Leu Gly Gly Arg Leu Leu Gly Gln Ser Ala Ala Ser Cys His His
                165                 170                 175
```

```
Ala Tyr Ile Val Leu Cys Ile Glu Asn Ser Phe Met Thr Ala Ser Xaa
                180                 185                 190
```

```
<210> SEQ ID NO 11
<211> LENGTH: 193
<212> TYPE: PRT
<213> ORGANISM: Homo sapiens

<400> SEQUENCE: 11
```

```
Met Gly Gly Ser His His His His His Ser His Arg Asp Phe Gln
1               5                   10                  15

Pro Val Leu His Leu Val Ala Leu Asn Ser Pro Leu Ser Gly Gly Met
                20                  25                  30

Arg Gly Ile Arg Gly Ala Asp Phe Gln Cys Phe Gln Gln Ala Arg Ala
                35                  40                  45

Val Gly Leu Ala Gly Thr Phe Arg Ala Phe Leu Ser Ser Arg Leu Gln
        50                  55                  60

Asp Leu Tyr Ser Ile Val Arg Arg Ala Asp Arg Ala Ala Val Pro Ile
65                  70                  75                  80

Val Asn Leu Lys Asp Glu Leu Leu Phe Pro Ser Trp Glu Ala Leu Phe
                85                  90                  95

Ser Gly Ser Glu Gly Pro Leu Lys Pro Gly Ala Arg Ile Phe Ser Phe
                100                 105                 110

Asn Gly Lys Asp Val Leu Thr His Pro Thr Trp Pro Gln Lys Ser Val
                115                 120                 125

Trp His Gly Ser Asp Pro Asn Gly Arg Arg Leu Thr Glu Ser Tyr Cys
        130                 135                 140

Glu Thr Trp Arg Thr Glu Ala Pro Ser Ala Thr Gly Gln Ala Tyr Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Lys
                180                 185                 190

Cys
```

```
<210> SEQ ID NO 12
<211> LENGTH: 184
<212> TYPE: PRT
<213> ORGANISM: Homo sapiens
<220> FEATURE:
<221> NAME/KEY: MISC_FEATURE
<222> LOCATION: (76)..(76)
<223> OTHER INFORMATION: X1 may be any naturally occurring amino acid
      other than lysine
<220> FEATURE:
<221> NAME/KEY: MISC_FEATURE
<222> LOCATION: (96)..(96)
<223> OTHER INFORMATION: X2 may be any naturally occurring amino acid
      other than lysine
<220> FEATURE:
<221> NAME/KEY: MISC_FEATURE
<222> LOCATION: (107)..(107)
<223> OTHER INFORMATION: X3 may be any naturally occurring amino acid
      other than lysine
<220> FEATURE:
<221> NAME/KEY: MISC_FEATURE
<222> LOCATION: (118)..(118)
<223> OTHER INFORMATION: X4 may be any naturally occurring amino acid
      other than lysine
<220> FEATURE:
<221> NAME/KEY: MISC_FEATURE
<222> LOCATION: (184)..(184)
<223> OTHER INFORMATION: X5 may be any naturally occurring amino acid
      other than lysine
```

<400> SEQUENCE: 12

Met His Ser His Arg Asp Phe Gln Pro Val Leu His Leu Val Ala Leu
1               5                   10                  15

Asn Ser Pro Leu Ser Gly Gly Met Arg Gly Ile Arg Gly Ala Asp Phe
            20                  25                  30

Gln Cys Phe Gln Gln Ala Arg Ala Val Gly Leu Ala Gly Thr Phe Arg
        35                  40                  45

Ala Phe Leu Ser Ser Arg Leu Gln Asp Leu Tyr Ser Ile Val Arg Arg
50                  55                  60

Ala Asp Arg Ala Ala Val Pro Ile Val Asn Leu Xaa Asp Glu Leu Leu
65                  70                  75                  80

Phe Pro Ser Trp Glu Ala Leu Phe Ser Gly Ser Glu Gly Pro Leu Xaa
                85                  90                  95

Pro Gly Ala Arg Ile Phe Ser Phe Asn Gly Xaa Asp Val Leu Thr His
            100                 105                 110

Pro Thr Trp Pro Gln Xaa Ser Val Trp His Gly Ser Asp Pro Lys Gly
        115                 120                 125

Arg Arg Leu Thr Glu Ser Tyr Cys Glu Thr Trp Arg Thr Glu Ala Pro
130                 135                 140

Ser Ala Thr Gly Gln Ala Tyr Ser Leu Leu Gly Gly Arg Leu Leu Gly
145                 150                 155                 160

Gln Ser Ala Ala Ser Cys His His Ala Tyr Ile Val Leu Cys Ile Glu
                165                 170                 175

Asn Ser Phe Met Thr Ala Ser Xaa
            180

<210> SEQ ID NO 13
<211> LENGTH: 192
<212> TYPE: PRT
<213> ORGANISM: Homo sapiens
<220> FEATURE:
<221> NAME/KEY: MISC_FEATURE
<222> LOCATION: (84)..(84)
<223> OTHER INFORMATION: X1 may be any naturally occurring amino acid
      other than lysine
<220> FEATURE:
<221> NAME/KEY: MISC_FEATURE
<222> LOCATION: (104)..(104)
<223> OTHER INFORMATION: X2 may be any naturally occurring amino acid
      other than lysine
<220> FEATURE:
<221> NAME/KEY: MISC_FEATURE
<222> LOCATION: (115)..(115)
<223> OTHER INFORMATION: X3 may be any naturally occurring amino acid
      other than lysine
<220> FEATURE:
<221> NAME/KEY: MISC_FEATURE
<222> LOCATION: (126)..(126)
<223> OTHER INFORMATION: X4 may be any naturally occurring amino acid
      other than lysine
<220> FEATURE:
<221> NAME/KEY: MISC_FEATURE
<222> LOCATION: (192)..(192)
<223> OTHER INFORMATION: X5 may be any naturally occurring amino acid
      other than lysine

<400> SEQUENCE: 13

Met Gly Gly Ser His His His His His Ser His Arg Asp Phe Gln
1               5                   10                  15

Pro Val Leu His Leu Val Ala Leu Asn Ser Pro Leu Ser Gly Gly Met
            20                  25                  30

Arg Gly Ile Arg Gly Ala Asp Phe Gln Cys Phe Gln Gln Ala Arg Ala

```
                35                  40                  45
Val Gly Leu Ala Gly Thr Phe Arg Ala Phe Leu Ser Ser Arg Leu Gln
    50                  55                  60

Asp Leu Tyr Ser Ile Val Arg Arg Ala Asp Arg Ala Ala Val Pro Ile
65                  70                  75                  80

Val Asn Leu Xaa Asp Glu Leu Leu Phe Pro Ser Trp Glu Ala Leu Phe
                85                  90                  95

Ser Gly Ser Glu Gly Pro Leu Xaa Pro Gly Ala Arg Ile Phe Ser Phe
                100                 105                 110

Asn Gly Xaa Asp Val Leu Thr His Pro Thr Trp Pro Gln Xaa Ser Val
            115                 120                 125

Trp His Gly Ser Asp Pro Lys Gly Arg Arg Leu Thr Glu Ser Tyr Cys
        130                 135                 140

Glu Thr Trp Arg Thr Glu Ala Pro Ser Ala Thr Gly Gln Ala Tyr Ser
145                 150                 155                 160

Leu Leu Gly Gly Arg Leu Leu Gly Gln Ser Ala Ala Ser Cys His His
                165                 170                 175

Ala Tyr Ile Val Leu Cys Ile Glu Asn Ser Phe Met Thr Ala Ser Xaa
            180                 185                 190

<210> SEQ ID NO 14
<211> LENGTH: 8
<212> TYPE: PRT
<213> ORGANISM: Artificial Sequence
<220> FEATURE:
<223> OTHER INFORMATION: Fragment

<400> SEQUENCE: 14

Gly Gly Ser His His His His
1               5

<210> SEQ ID NO 15
<211> LENGTH: 9
<212> TYPE: PRT
<213> ORGANISM: Artificial Sequence
<220> FEATURE:
<223> OTHER INFORMATION: Fragment

<400> SEQUENCE: 15

Met Gly Gly Ser His His His His
1               5
```

The invention claimed is:

1. An endostatin analogue-PEG coupled complex, wherein the endostatin analogue has a lysine residue at a position corresponding to position 96 of the amino acid sequence SEQ ID NO. 1 of naturally occurring endostatin, and no lysine residue at any other position; and the endostatin analogue is coupled to PEG only at the lysine residue or is coupled to PEG at N-terminus and the lysine residue.

2. The coupled complex according to claim 1, wherein the endostatin analogue is formed by mutation of lysine residues at positions 76, 107, 118 and 184 of the amino acid sequence SEQ ID NO. 1 of naturally occurring endostatin.

3. The coupled complex according to claim 1, wherein the endostatin analogue is a functional variant of endostatin having an amino acid sequence inserted at its N-terminus.

4. The coupled complex according to claim 3, wherein the endostatin analogue is formed by mutation of the lysine residues at positions 76, 107, 118 and 184 of the amino acid sequence SEQ ID NO. 1 of naturally occurring endostatin, and insertion of GGSHHHHH (SEQ ID NO. 14) between methionine M and histidine H at its N-terminus.

5. The coupled complex according to claim 3, wherein the amino acid sequence inserted at N-terminus is MGGSHHHHH (SEQ ID NO. 15).

6. The coupled complex according to claim 2, wherein the lysine residues at positions 76, 107, 118 and 184 of the amino acid sequence SEQ ID NO. 1 of naturally occurring endostatin are mutated to X1, X3, X4 and X5, respectively, wherein X1, X3, X4 or X5 is independently any one of arginine, histidine, glutamic acid and aspartic acid.

7. The coupled complex according to claim 1, wherein endostatin analogue is coupled to PEG via covalent bond.

8. The coupled complex according to claim 1, wherein the PEG has an average molecular weight between 5,000 and 40,000 Daltons.

9. The coupled complex according to claim 1, wherein the PEG is monomethoxy polyethylene glycol, monoglucose polyethylene glycol or monogalactose polyethylene glycol.

10. The coupled complex according to claim 1, wherein the coupling reaction between PEG and the amino group of endostatin analogue is carried out by using monomethoxy polyethylene glycol propionaldehyde (mPEG-ALD), monomethoxy polyethylene glycol butyraldehyde (mPEG-ButyrALD), monomethoxy polyethylene glycol succinimidyl carbonate (mPEG-SC), monomethoxy polyethylene glycol succinimidyl acetate (mPEG-SCM), monomethoxy polyethylene glycol succinimidyl propionate (mPEG-SPA), monomethoxy polyethene glycol succinimidyl butyrate (mPEG-SBA), monomethoxy polyethylene glycol succinimidyl α-methylbutyrate (mPEG-SMA), monomethoxy polyethylene glycol N-hydroxylsuccinimide (mPEG-NHS).

11. A pharmaceutical composition comprising the coupled complex according to claim 1 and optionally a pharmaceutically acceptable carrier.

12. A method for treating a tumor, comprising administering to a patient the coupled complex according to claim 1.

13. The coupled complex according to claim 4, wherein the lysine residues at positions 76, 107, 118 and 184 of the amino acid sequence SEQ ID NO. 1 of naturally occurring endostatin are mutated to X1, X3, X4 and X5, respectively, wherein X1, X3, X4 or X5 is independently any one of arginine, histidine, glutamic acid and aspartic acid.

14. The coupled complex according to claim 3, wherein endostatin analogue is coupled to PEG via covalent bond.

15. The coupled complex according to claim 3, wherein the PEG has an average molecular weight between 5,000 and 40,000 Daltons.

16. The coupled complex according to claim 3, wherein the PEG is monomethoxy polyethylene glycol, monoglucose polyethylene glycol or monogalactose polyethylene glycol.

17. The coupled complex according to claim 3, wherein the coupling reaction between PEG and the amino group of endostatin analogue is carried out by using monomethoxy polyethylene glycol propionaldehyde (mPEG-ALD), monomethoxy polyethylene glycol butyraldehyde (mPEG-ButyrALD), monomethoxy polyethylene glycol succinimidyl carbonate (mPEG-SC), monomethoxy polyethylene glycol succinimidyl acetate (mPEG-SCM), monomethoxy polyethylene glycol succinimidyl propionate (mPEG-SPA), monomethoxy polyethene glycol succinimidyl butyrate (mPEG-SBA), monomethoxy polyethylene glycol succinimidyl a-methylbutyrate (mPEG-SMA), monomethoxy polyethylene glycol N-hydroxylsuccinimide (mPEG-NHS).

18. The pharmaceutical composition according to claim 11, wherein the endostatin analogue is a functional variant of endostatin having an amino acid sequence inserted at its N-terminus.

19. The method according to claim 12, wherein the endostatin analogue is a functional variant of endostatin having an amino acid sequence inserted at its N-terminus.

* * * * *